US007883710B2

(12) United States Patent
Beall et al.

(10) Patent No.: US 7,883,710 B2
(45) Date of Patent: *Feb. 8, 2011

(54) PEPTIDE VACCINES AGAINST GROUP A STREPTOCOCCI

(75) Inventors: Bernard W. Beall, Doraville, GA (US); George M. Carlone, Stone Mountain, GA (US); Jacquelyn S. Sampson, College Park, GA (US); Edwin W. Ades, Atlanta, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 114 days.

This patent is subject to a terminal disclaimer.

(21) Appl. No.: 12/144,461

(22) Filed: Jun. 23, 2008

(65) Prior Publication Data

US 2008/0279880 A1    Nov. 13, 2008

Related U.S. Application Data

(63) Continuation of application No. 10/477,955, filed as application No. PCT/US02/15909 on May 20, 2002, now Pat. No. 7,407,664.

(60) Provisional application No. 60/291,835, filed on May 18, 2001.

(51) Int. Cl.
*A61K 39/09* (2006.01)
*C07H 21/04* (2006.01)
*C07K 4/04* (2006.01)
*C12P 21/06* (2006.01)

(52) U.S. Cl. ............. 424/244.1; 424/234.1; 424/184.1; 530/300; 530/350; 536/23.1; 536/23.5; 536/23.7; 435/69.3; 435/69.7; 435/252.1; 435/320.1; 435/69.1

(58) Field of Classification Search ........................ None
See application file for complete search history.

(56) References Cited

U.S. PATENT DOCUMENTS

| 3,710,795 | A | 1/1973 | Higuchi et al. | |
|---|---|---|---|---|
| 6,063,386 | A | 5/2000 | Dale et al. | |
| 6,716,433 | B1 | 4/2004 | Dale | |
| 7,407,664 | B2 * | 8/2008 | Beall et al. | 424/244.1 |

FOREIGN PATENT DOCUMENTS

| WO | 94/06465 | 3/1994 |
|---|---|---|
| WO | 99/13084 | 3/1999 |

OTHER PUBLICATIONS

Beachey et al., "Human Immune Response to Immunization with a Structurally Defined Polypeptide Fragment of Streptococcal M Protein," *J. Exp. Med.*, 150:862-877 (1979).

Beachey et al., "Opsonic Antibodies Evoked by Hybrid Peptide Copies of Types 5 and 24 Streptococcal M Proteins Synthesized in Tandem," *J. Exp. Med.*, 165:1451-1458 (1986).

Beachey et al., "Protective and Nonprotective Epitopes of Chemically Synthesized Peptides of the $NH_2$-Thermal Region of Type 6 Streptococcal M Protein," *The Journal of Immunology*, 136(6):2287-2292 (1986).

Beall et al., "Streptococcal emm types associated with T-agglutination types and the use of conserved emm restriction fragment patters for subtyping group A Streptococci," *J. Med. Micro.*, 47:1-6 (1998).

Beall et al., "Survey of emm Gene Sequences and T-Antigen Types from Systemic Streptococcus pyogenes Infection Isolates Collected in San Francisco, California; Atlanta, Georgia; and Connecticut in 1994 and 1995," *J. Clin. Microbio.l*, 35(5):1231-1235 (1997).

Brandt and Good, "Vaccine Strategies to Prevent Rheumatic Fever," *Immunol. Res.*, 19(1):89-1031 (1999).

Brandt et al., "Protective and Nonprotective Epitopes from Amino termini of M Proteins from Australian Aboriginal Isolates and Reference Strains of Group A Streptococci," *Infection and Immunity*, 68(12):6587-6594 (2000).

Dale et al., "Hyuaronated Capsule and Surface M Protein in Resistance to Opsonization of Group A Streptococci," Infect. Immun., 64(5):1495-1501(1996).

Dale et al., "Passive Protection of Mice against Group A Streptococcal Pharyngeal Infection by Lipoteichoic Acid, " *J. Infect. Dis.*, 169:319-323 (1994).

Davies et al., "Invasive group A streptococcal infections in Ontario, Canada, Ontario group A streptococcal study group," *N. Engl. J. Med.*, 335(8):547-554 (1996).

Fischetti, "Streptococcal M Protein: Molecular Design and Biological Behavior," *Clin. Microbiol.*, 2(3):285-314 (1989).

Ji et al., "Intranasal Immunization with C5a peptidase Prevents Nasopharyngeal Colonization of Mice by Group A Streptococcus," *Infect. Immun.*, 65(6):2080-2087 (1997).

(Continued)

*Primary Examiner*—Larry R Helms
*Assistant Examiner*—Padma V Baskar
(74) *Attorney, Agent, or Firm*—Klarquist Sparkman, LLP

(57) ABSTRACT

This invention, in one aspect, relates to synthetic immunoreactive peptides. These peptides are approximately 20-25 amino acids in length which are portions of the N termini of the M proteins of the most prevalent United States (U.S.) Group A *Streptococcus* (GAS) serotypes. At least some of the synthetic peptides can be recognized by M type-specific antibodies and are capable of eliciting functional opsonic antibodies and/or anti-attachment antibodies without eliciting tissue cross-reactive antibodies. In another aspect, it relates to compositions or vaccines comprising these synthetic serotype-specific peptides, including polypeptides and proteins. The invention may also be isolated antibodies which are raised in response to the peptides, compositions or vaccines. The invention further relates to kits for using the peptides, compositions, or antibodies. In still further aspects, the invention also relates to methods for using the peptides, compositions, vaccines, or antibodies and methods for tailoring vaccines.

23 Claims, 1 Drawing Sheet

OTHER PUBLICATIONS

Kapur et al., "Vaccination with streptococcal extracellular cysteine protease (interleukin-1β convertase) protects mice against challenge with heterologous group A streptococci," *Microb. Pathogen*, 16:443-450 (1994).

Lancefield, "Current knowledge of the type-specific M antigens of group A streptococci," *J. Immun.*, 89:307-313 (1962).

Lancefield, "Persistence of type-specific antibodies in man following infection with group A streptococci," *J. Exp. Med.*, 110:271-292 (1959).

Musser et al., "Genetic Diversity and Relationships among Streptococcus pyogenes Strains Expressing Serotype M1 Protein: Recent intercontinental Spread of a Subclone Causing Episodes of Invasive Disease," *Infection and Immunity*, 63(3):994-1003 (1995).

Salvadori et al., "Group A Streptococcus-Liposome ELISA Antibody Titers to Group A Polysaccharide and Opsonophagocytic Capabilities of the Antibodies," *J. Infect. Dis.*, 171:593-600 (1995).

Veasy et al., "Resurgence of acute rheumatic fever in the intermountain region of the United States," *N. Engl. J. Med.*, 316(8):42-47 (1987).

\* cited by examiner

Population-based U.S. sterile site isolate distribution among the 24 most prevalent *emm* types [2321 (88.9%) of the entire 2612 isolate sample]

SEQUENCE LISTING

<160> NUMBER OF SEQ ID NOS: 138

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 1

Cys Asn Gly Asp Gly Asn Pro Arg Glu Val Ile Glu Asp Leu Ala Ala
1               5                   10                  15

Asn Asn Pro Ala Ile Gln
            20

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 2

Cys Ile Gln Asn Ile Arg Leu Arg His Glu Asn Lys Asp Leu Lys Ala
1               5                   10                  15

Arg Leu Glu Asn Ala
            20

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 3

Cys Ile Arg Leu Arg His Glu Asn Lys Asp Leu Lys Ala Arg Leu Glu
1               5                   10                  15

Asn Ala Met Glu Val
            20

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 4

Cys Asn Gly Asp Gly Asn Pro Arg Glu Val Ile Glu Asp Leu Ala Ala
1               5                   10                  15

Asn Asn Pro Ala Met Glu
            20

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence; NOTE =

Synthetic Construct

<400> SEQUENCE: 5

Cys Ile Arg Asn Ile Arg Leu Arg His Glu Asn Lys Asp Leu Lys Ala
1               5                   10                  15

Arg Leu Glu Asn Ala
            20

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 6

Cys Asn Gly Asp Gly Asn Pro Arg Glu Val Ile Glu Asp Leu Ala Ala
1               5                   10                  15

Asn Asn Pro Val Ile Gln
            20

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 7

Cys Asn Gly Asp Gly Asn Pro Arg Val Val Ile Glu Asp Leu Ala Ala
1               5                   10                  15

Asn Asn Pro Ala Ile Gln
            20

<210> SEQ ID NO 8
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 8

Cys Ile Arg Leu Arg His His Glu Asn Lys Asp Leu Lys Ala Arg Leu
1               5                   10                  15

Glu Asn Ala Met Glu Val
            20

<210> SEQ ID NO 9
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 9

Cys Asn Ser Lys Asn Pro Val Pro Val Lys Lys Glu Ala Lys Leu Ser
1               5                   10                  15

Glu Ala Glu Leu His Asp Lys
            20

```
<210> SEQ ID NO 10
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 10

Cys Lys Lys Glu Ala Lys Leu Ser Glu Ala Glu Leu His Asp Lys Ile
1               5                   10                  15

Lys Asn Leu Glu Glu Glu Lys
            20

<210> SEQ ID NO 11
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 11

Cys Glu Leu His Asp Lys Ile Lys Asn Leu Glu Glu Glu Lys Ala Glu
1               5                   10                  15

Leu Phe Glu Lys Leu Asp
            20

<210> SEQ ID NO 12
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 12

Cys Glu Leu Phe Glu Lys Leu Asp Lys Val Glu Glu His Lys Lys
1               5                   10                  15

Val Glu Glu Glu His Lys Lys
            20

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 13

Cys Asp Ala Arg Ser Val Asn Gly Glu Phe Pro Arg His Val Lys Leu
1               5                   10                  15

Lys Asn Glu Ile Glu
            20

<210> SEQ ID NO 14
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 14

Cys Gly Glu Phe Pro Arg His Val Lys Leu Lys Asn Glu Ile Glu Asn
```

```
                1               5                   10                  15

Leu Leu Asp Gln Val
            20

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 15

Cys Leu Asp Gln Val Thr Gln Leu Tyr Thr Lys His Asn Ser Asn Tyr
1               5                   10                  15

Gln Gln Tyr Asn Ala
            20

<210> SEQ ID NO 16
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 16

Cys Leu Asp Gln Val Thr Gln Leu Tyr Asn Lys His Asn Ser Asn Tyr
1               5                   10                  15

Gln Gln Tyr Ser Ala
            20

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 17

Cys Leu Asp Gln Val Thr Gln Leu Tyr Thr Lys His Asn Ser Asn Tyr
1               5                   10                  15

Gln Gln Tyr Ser Ala
            20

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 18

Cys Leu Asn Gln Val Thr Gln Leu Tyr Thr Lys His Asn Ser Asn Tyr
1               5                   10                  15

Gln Gln Tyr Asn Ala
            20

<210> SEQ ID NO 19
<211> LENGTH: 21
<212> TYPE: PRT
<213> ORGANISM: Artificial Sequence
<220> FEATURE:
```

```
<223> OTHER INFORMATION: Description of Artificial Sequence; NOTE =
      Synthetic Construct

<400> SEQUENCE: 19

Cys Leu Ala Gln Val Thr Gln Leu Tyr Thr Lys His Asn Ser Asn Tyr
1               5                   10                  15

Gln Gln Tyr Asn Ala
            20

<210> SEQ ID NO 20
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 20

Cys Leu Asn Gln Val Thr Gln Leu His Thr Lys His Asn Ser Asn Tyr
1               5                   10                  15

Gln Gln Tyr Asn Ala
            20

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 21

Cys Arg Ser Asp Ala Arg Ser Val Asn Gly Glu Phe Pro Arg His Val
1               5                   10                  15

Lys Leu Lys Asn Glu
            20

<210> SEQ ID NO 22
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 22

Cys Gln Leu Tyr Thr Lys His Ile Tyr Thr Lys His Asn Ser Asn Tyr
1               5                   10                  15

Gln Gln Tyr Asn Ala Gln
            20

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 23

Cys Thr Gln Leu Tyr Thr Lys His Asn Ser Asn Tyr Gln Gln Tyr Asn
1               5                   10                  15

Ala Gln Ala Gly Arg
            20
```

```
<210> SEQ ID NO 24
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 24

Cys Ala Glu Ile Lys Lys Pro Gln Ala Asp Ser Ala Trp Asn Trp Pro
1               5                   10                  15

Lys Glu Tyr Asn Ala
            20

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 25

Cys Asp Ser Ala Trp Asn Trp Pro Lys Glu Tyr Asn Ala Leu Leu Lys
1               5                   10                  15

Glu Asn Glu Glu Leu
            20

<210> SEQ ID NO 26
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 26

Cys Lys Glu Asn Glu Glu Leu Lys Val Glu Arg Glu Lys Tyr Leu Ser
1               5                   10                  15

Tyr Ala Asp Asp Lys
            20

<210> SEQ ID NO 27
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 27

Cys Glu Glu Leu Lys Val Glu Arg Glu Lys Tyr Leu Ser Tyr Ala Asp
1               5                   10                  15

Asp Lys Glu Lys Asp Pro Gln
            20

<210> SEQ ID NO 28
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 28
```

```
Cys Ala Gly Gln Ser Ala Pro Lys Gly Thr Asn Val Ser Ala Asp Leu
1               5                   10                  15

Tyr Asn Ser Leu Trp Asp Glu
                20

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 29

Cys Lys Gly Thr Asn Val Ser Ala Asp Leu Tyr Asn Ser Leu Trp Asp
1               5                   10                  15

Glu Asn Lys Thr
                20

<210> SEQ ID NO 30
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 30

Cys Asp Glu Asn Lys Thr Leu Arg Glu Lys Gln Glu Glu Tyr Ile Thr
1               5                   10                  15

Lys Ile Gln Asn Glu
                20

<210> SEQ ID NO 31
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 31

Cys Thr Glu Val Lys Ala Ala Gly Gln Ser Ala Pro Lys Gly Thr Asn
1               5                   10                  15

Val Ser Ala Asp Leu
                20

<210> SEQ ID NO 32
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 32

Cys Asp His Ser Asp Leu Val Ala Glu Lys Gln Arg Leu Glu Asp Leu
1               5                   10                  15

Gly Gln Lys Phe Glu
                20

<210> SEQ ID NO 33
<211> LENGTH: 21
<212> TYPE: PRT
<213> ORGANISM: Artificial Sequence
```

```
<220> FEATURE:
<223> OTHER INFORMATION: Description of Artificial Sequence; NOTE =
      Synthetic Construct

<400> SEQUENCE: 33

Cys Ala Glu Lys Gln Arg Leu Glu Asp Leu Gly Gln Lys Phe Glu Arg
1               5                   10                  15

Leu Lys Gln Arg Ser
            20

<210> SEQ ID NO 34
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 34

Cys Leu Glu Asp Leu Gly Gln Lys Phe Glu Arg Leu Lys Gln Arg Ser
1               5                   10                  15

Glu Leu Tyr Leu Gln
            20

<210> SEQ ID NO 35
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 35

Cys Lys Phe Glu Arg Leu Lys Gln Arg Ser Glu Leu Tyr Leu His Gln
1               5                   10                  15

Tyr Tyr Asp Asn Lys
            20

<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 36

Cys Lys Phe Glu Arg Leu Lys Arg Arg Ser Glu Leu Tyr Leu Gln Gln
1               5                   10                  15

Tyr Tyr Asp Asn Lys
            20

<210> SEQ ID NO 37
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 37

Cys Lys Gln Arg Ser Glu Leu Tyr Leu Gln Gln Tyr Tyr Asp Asn Lys
1               5                   10                  15

Ser Asn Arg Tyr Lys
            20
```

```
<210> SEQ ID NO 38
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 38

Cys Ser Glu Leu Tyr Leu Gln Gln Tyr Tyr Asp Asn Lys Ser Asn Gly
1               5                   10                  15

Tyr Lys Gly Asp Trp
            20

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 39

Cys Glu Ser Ser Asn Asn Ala Glu Ser Ser Asn Ile Ser Gln Glu Ser
1               5                   10                  15

Lys Leu Ile Asn Thr
            20

<210> SEQ ID NO 40
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 40

Cys Glu Ser Ser Asn Ile Ser Gln Glu Ser Lys Leu Ile Asn Thr Leu
1               5                   10                  15

Thr Asp Glu Asn Glu Lys
            20

<210> SEQ ID NO 41
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 41

Cys Glu Ser Lys Leu Ile Asn Thr Leu Thr Asp Glu Asn Glu Lys Leu
1               5                   10                  15

Arg Glu Glu Leu Gln Gln
            20

<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 42
```

```
Cys Asn Thr Leu Asn Thr Leu Thr Asp Glu Asn Glu Lys Leu Arg Glu
1               5                   10                  15

Glu Leu Gln Gln
            20

<210> SEQ ID NO 43
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 43

Cys Glu Ser Ser Asn Ile Ser Gln Glu Ser Lys Leu Ile Asn Thr Leu
1               5                   10                  15

Thr Asp Glu Asn Glu Lys
            20

<210> SEQ ID NO 44
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 44

Cys Glu Lys Leu Arg Glu Glu Leu Gln Gln Tyr Tyr Ala Leu Ser Asp
1               5                   10                  15

Ala Lys Glu Glu Glu
            20

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 45

Cys Ala Glu Ser Pro Lys Ser Thr Glu Thr Ser Ala Asn Gly Ala Asp
1               5                   10                  15

Lys Leu Ala Asp
            20

<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 46

Cys Lys Ser Thr Glu Thr Ser Ala Asn Gly Ala Asp Lys Leu Ala Asp
1               5                   10                  15

Ala Tyr Asn Thr Leu
            20

<210> SEQ ID NO 47
<211> LENGTH: 21
<212> TYPE: PRT
```

-continued

```
<213> ORGANISM: Artificial Sequence
<220> FEATURE:
<223> OTHER INFORMATION: Description of Artificial Sequence; NOTE =
      Synthetic Construct

<400> SEQUENCE: 47

Cys Asp Lys Leu Ala Asp Ala Tyr Asn Thr Leu Leu Thr Glu His Glu
1               5                   10                  15

Lys Leu Arg Asp Glu
            20

<210> SEQ ID NO 48
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 48

Cys Thr Glu His Glu Lys Leu Arg Asp Glu Tyr Tyr Thr Leu Ile Asp
1               5                   10                  15

Ala Lys Leu Glu Glu Lys
            20

<210> SEQ ID NO 49
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 49

Cys Thr Glu His Glu Lys Leu Arg Asp Glu Tyr Tyr Thr Leu Ile Asp
1               5                   10                  15

Ala Lys Glu Glu Glu
            20

<210> SEQ ID NO 50
<211> LENGTH: 25
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 50

Cys Glu Gly Val Ser Val Gly Ser Asp Ala Ser Leu His Asn Arg Ile
1               5                   10                  15

Thr Asp Leu Glu Glu Glu Arg Glu Lys
            20                  25

<210> SEQ ID NO 51
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 51

Cys Ser Asp Ala Ser Leu His Asn Arg Ile Thr Asp Leu Glu Glu Glu
1               5                   10                  15

Arg Glu Lys Leu Leu Asn Lys
```

20

<210> SEQ ID NO 52
<211> LENGTH: 24
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 52

Cys Asp Leu Glu Glu Glu Arg Glu Lys Leu Leu Asn Lys Leu Asp Lys
1               5                   10                  15

Val Glu Glu Glu His Lys Lys Asp
            20

<210> SEQ ID NO 53
<211> LENGTH: 22
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 53

Cys Asp Leu Glu Glu Glu Arg Gly Lys Leu Leu Asn Lys Leu Asp Lys
1               5                   10                  15

Val Glu Glu Glu His Lys
            20

<210> SEQ ID NO 54
<211> LENGTH: 21
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 54

Cys Leu Asn Lys Leu Asp Lys Val Glu Glu His Lys Lys Asp His
1               5                   10                  15

Glu Gln Leu Glu Lys
            20

<210> SEQ ID NO 55
<211> LENGTH: 22
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 55

Cys Asp Ser Asp Asn Ile Asn Arg Ser Val Ser Val Lys Asp Asn Glu
1               5                   10                  15

Lys Glu Leu His Asn Lys
            20

<210> SEQ ID NO 56
<211> LENGTH: 23
<212> TYPE: PRT
<213> ORGANISM: Artificial Sequence
<220> FEATURE:
<223> OTHER INFORMATION: Description of Artificial Sequence; NOTE = Synthetic Construct -continued

```
<400> SEQUENCE: 56

Cys Asp Asn Ile Asn Arg Ser Val Ser Val Lys Asp Asn Glu Lys Glu
1               5                   10                  15

Leu His Asn Lys Ile Ala Asp
            20

<210> SEQ ID NO 57
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 57

Cys Ser Val Lys Asp Asn Glu Lys Glu Leu His Asn Lys Ile Ala Asp
1               5                   10                  15

Leu Glu Glu Glu Arg
            20

<210> SEQ ID NO 58
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 58

Cys Glu Leu His Asn Glu Ile Ala Asp Leu Glu Glu Glu Arg Gly Glu
1               5                   10                  15

His Leu Asp Lys Ile Asp
            20

<210> SEQ ID NO 59
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 59

Cys Glu Leu His Asn Lys Ile Ala Asp Leu Glu Glu Glu Arg Gly Ala
1               5                   10                  15

His Leu Asp Lys Ile Asp
            20

<210> SEQ ID NO 60
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 60

Cys Asp Ser Asp Asn Ile Asn Arg Phe Val Ser Val Lys Asp Asn Glu
1               5                   10                  15

Lys Glu Leu His Asn
            20

<210> SEQ ID NO 61
<211> LENGTH: 21
```

```
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 61

Cys Asp Ser Asp Asn Ser Asp Asn Ile Asn Arg Ser Val Ser Val Lys
1               5                   10                  15

Asp Asn Glu Lys Glu
            20

<210> SEQ ID NO 62
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 62

Cys Leu Glu Glu Glu Arg Gly Glu His Leu Asp Lys Ile Asp Glu Leu
1               5                   10                  15

Lys Glu Glu Leu Lys
            20

<210> SEQ ID NO 63
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 63

Cys Asn Ser Lys Asn Pro Ala Pro Ala Pro Ser Ala Val Pro Val
1               5                   10                  15

Lys Lys Glu Ala Thr Lys
            20

<210> SEQ ID NO 64
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 64

Cys Val Pro Val Lys Lys Glu Ala Thr Lys Leu Ser Glu Ala Glu Leu
1               5                   10                  15

Tyr Asn Lys Ile Gln
            20

<210> SEQ ID NO 65
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 65

Cys Lys Lys Glu Ala Thr Lys Leu Ser Glu Ala Glu Leu Tyr Asn Lys
1               5                   10                  15
```

Ile Gln Glu Leu Glu Glu
            20

<210> SEQ ID NO 66
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 66

Cys Asn Ser Lys Asn Pro Ala Pro Ala Pro Val Pro Val Lys Lys
1               5                   10                  15

Glu Ala Thr Lys Leu
            20

<210> SEQ ID NO 67
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 67

Cys Asn Ser Lys Asn Pro Ala Pro Ala Val Pro Val Lys Lys Glu Ala
1               5                   10                  15

Thr Lys Leu Ser Glu
            20

<210> SEQ ID NO 68
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 68

Cys Ala Glu Leu Tyr Asn Lys Ile Gln Glu Leu Glu Glu Gly Lys Ala
1               5                   10                  15

Glu Leu Phe Asp Lys
            20

<210> SEQ ID NO 69
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 69

Cys Arg Val Phe Pro Arg Gly Thr Val Glu Asn Pro Asp Lys Ala Arg
1               5                   10                  15

Glu Leu Leu Asn Lys
            20

<210> SEQ ID NO 70
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

```
<400> SEQUENCE: 70

Cys Arg Gly Thr Val Glu Asn Pro Asp Lys Ala Arg Glu Leu Leu Asn
1               5                   10                  15

Lys Tyr Asp Val Glu Asn
            20

<210> SEQ ID NO 71
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 71

Cys Glu Asn Pro Asp Lys Ala Arg Glu Leu Leu Asn Lys Tyr Asp Val
1               5                   10                  15

Glu Asn Ser Met Leu Gln
            20

<210> SEQ ID NO 72
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 72

Cys Glu Asn Ser Met Leu Gln Ala Asn Asn Asp Asn Leu Thr Asp Gln
1               5                   10                  15

Asn Lys Asn Leu Thr Asp
            20

<210> SEQ ID NO 73
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 73

Cys Asn Ser Met Leu Gln Ala Asn Asn Asp Lys Leu Thr Thr Glu Asn
1               5                   10                  15

Lys Asn Leu Thr Asp
            20

<210> SEQ ID NO 74
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 74

Cys Asp Ser Ser Arg Asp Ile Thr Glu Ala Gly Val Ser Lys Phe
1               5                   10                  15

Trp Lys Ser Lys Phe Asp
            20

<210> SEQ ID NO 75
```

<211> LENGTH: 22
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 75

Cys Arg Asp Ile Thr Glu Ala Gly Val Ser Lys Phe Trp Lys Ser Lys
1               5                   10                  15

Phe Asp Ala Glu Gln Asn
            20

<210> SEQ ID NO 76
<211> LENGTH: 22
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 76

Cys Glu Ala Gly Val Ser Lys Phe Trp Lys Ser Lys Phe Asp Ala Glu
1               5                   10                  15

Gln Asn Arg Ala Asn Glu
            20

<210> SEQ ID NO 77
<211> LENGTH: 21
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 77

Cys Asp Ala Glu Gln Asn Arg Ala Asn Glu Leu Glu Lys Lys Leu Ser
1               5                   10                  15

Gly Tyr Glu Lys Asp
            20

<210> SEQ ID NO 78
<211> LENGTH: 19
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 78

Cys Glu Glu His Pro Asp Val Val Ala Ala Arg Glu Ser Val Leu Asn
1               5                   10                  15

Asn Val Arg

<210> SEQ ID NO 79
<211> LENGTH: 21
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 79

Cys His Pro Asp Val Val Ala Ala Arg Glu Ser Val Leu Asn Asn Val
1               5                   10                  15

Arg Val Pro Gly Thr
            20

<210> SEQ ID NO 80
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 80

Cys Arg Val Pro Gly Thr Leu Trp Leu Arg Gln Lys Glu Glu Asn Asp
1               5                   10                  15

Lys Leu Lys Leu Glu Lys
            20

<210> SEQ ID NO 81
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 81

Cys Leu Arg Gln Lys Glu Glu Asn Asp Lys Leu Lys Leu Glu Lys Lys
1               5                   10                  15

Gly Leu Glu Thr Glu
            20

<210> SEQ ID NO 82
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 82

Cys Glu Glu Glu Arg Thr Phe Thr Glu Leu Pro Tyr Glu Ala Arg Tyr
1               5                   10                  15

Lys Ala Trp Lys Ser Glu
            20

<210> SEQ ID NO 83
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 83

Cys Glu Leu Pro Tyr Glu Ala Arg Tyr Lys Ala Trp Lys Ser Glu Asn
1               5                   10                  15

Asp Glu Leu Arg Glu Asn
            20

<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct -continued

```
<400> SEQUENCE: 84

Cys Asn Asp Glu Leu Arg Glu Asn Tyr Arg Arg Thr Leu Asp Lys Phe
1               5                   10                  15

Asn Thr Glu Gln
            20

<210> SEQ ID NO 85
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 85

Cys Lys Ala Trp Lys Ser Glu Asn Asp Glu Leu Arg Glu Asn Tyr Arg
1               5                   10                  15

Lys Thr Leu Asp Lys
            20

<210> SEQ ID NO 86
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 86

Cys Arg Glu Asn Tyr Arg Arg Thr Leu Asp Lys Phe Asn Thr Glu Gln
1               5                   10                  15

Gly Lys Thr Thr Arg
            20

<210> SEQ ID NO 87
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 87

Cys Glu Glu His Glu Lys Val Thr Gln Ala Arg Glu Ala Val Ile Arg
1               5                   10                  15

Glu Met Gln Gln Arg
            20

<210> SEQ ID NO 88
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 88

Cys His Glu Lys Val Thr Gln Ala Arg Glu Ala Val Ile Arg Glu Met
1               5                   10                  15

Gln Gln Arg Gly Thr
            20

<210> SEQ ID NO 89
```

```
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 89

Cys Glu Met Gln Gln Arg Gly Thr Asn Phe Gly Pro Leu Leu Ala Ser
1               5                   10                  15

Thr Met Arg Asp Asn His
            20

<210> SEQ ID NO 90
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 90

Cys Asp Asp Arg Ser Val Ser Thr Asn Ser Gly Ser Val Ser Thr Pro
1               5                   10                  15

Tyr Asn Asn Leu Leu Asn Glu
            20

<210> SEQ ID NO 91
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 91

Cys Arg Ser Val Ser Thr Asn Ser Gly Ser Val Ser Thr Pro Tyr Asn
1               5                   10                  15

Asn Leu Leu Asn Glu
            20

<210> SEQ ID NO 92
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 92

Cys Glu Tyr Asp Asp Leu Leu Ala Lys His Gly Glu Leu Leu Ser Glu
1               5                   10                  15

Tyr Asp Ala Leu Lys
            20

<210> SEQ ID NO 93
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 93

Cys Asp Leu Leu Ala Lys His Gly Glu Leu Leu Ser Glu Tyr Asp Ala
1               5                   10                  15
```

-continued

Leu Lys Glu Lys Gln Asp Lys
            20

<210> SEQ ID NO 94
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 94

Cys Thr Val Thr Arg Gly Thr Ile Asn Asp Pro Gln Arg Ala Lys Glu
1               5                   10                  15

Ala Leu Asp Lys Tyr Glu
            20

<210> SEQ ID NO 95
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 95

Cys Asp Pro Gln Arg Ala Lys Glu Ala Leu Asp Lys Tyr Glu Leu Glu
1               5                   10                  15

Asn His Asp Leu Lys
            20

<210> SEQ ID NO 96
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 96

Cys Glu Asn His Asp Leu Lys Thr Lys Asn Glu Gly Leu Lys Thr Glu
1               5                   10                  15

Asn Glu Gly Leu Lys
            20

<210> SEQ ID NO 97
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 97

Cys Gln Arg Ala Lys Ala Ala Leu Asp Lys Tyr Glu Leu Glu Asn His
1               5                   10                  15

Asp Leu Lys Thr Lys Asn
            20

<210> SEQ ID NO 98
<211> LENGTH: 22
<212> TYPE: PRT
<213> ORGANISM: Artificial Sequence
<220> FEATURE:
<223> OTHER INFORMATION: Description of Artificial Sequence; NOTE =

Synthetic Construct

<400> SEQUENCE: 98

Cys Thr Val Thr Arg Gly Thr Val Asn Asp Pro Gln Arg Ala Lys Glu
1               5                   10                  15

Ala Leu Asp Lys Tyr Glu
            20

<210> SEQ ID NO 99
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 99

Cys Thr Val Thr Arg Gly Thr Val Asn Asp Pro Gln Arg Ala Lys Glu
1               5                   10                  15

Thr Leu Asp Lys Tyr Glu
            20

<210> SEQ ID NO 100
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 100

Cys Thr Val Thr Arg Gly Thr Ile Asn Asp Pro Gln Arg Ala Lys Glu
1               5                   10                  15

Val Ile Asp Lys Tyr Glu
            20

<210> SEQ ID NO 101
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 101

Cys Thr Val Thr Arg Ser Thr Ile Asn Asp Pro Gln Arg Ala Lys Glu
1               5                   10                  15

Ala Leu Asp Lys Tyr Glu
            20

<210> SEQ ID NO 102
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 102

Cys His Asp Leu Lys Thr Lys Asn Glu Gly Leu Lys Thr Glu Asn Glu
1               5                   10                  15

Gly Leu Lys Thr Glu Asn
            20

```
<210> SEQ ID NO 103
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 103

Cys Glu Glu Ala Ser Asn Asn Gly Gln Leu Thr Leu Gln His Lys Asn
1               5                   10                  15

Asn Ala Leu Thr Ser Glu
            20

<210> SEQ ID NO 104
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 104

Cys Gln His Lys Asn Asn Ala Leu Thr Ser Glu Asn Glu Ser Leu Arg
1               5                   10                  15

Arg Glu Lys Asp Arg
            20

<210> SEQ ID NO 105
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 105

Cys Glu Ser Leu Arg Arg Glu Lys Asp Arg Tyr Leu Tyr Glu Lys Glu
1               5                   10                  15

Glu Leu Glu Lys Lys
            20

<210> SEQ ID NO 106
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 106

Cys Arg Arg Glu Glu Lys Asp Arg Tyr Leu Tyr Glu Lys Glu Glu Leu
1               5                   10                  15

Glu Lys Lys Asn Lys
            20

<210> SEQ ID NO 107
<211> LENGTH: 20
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 107

Cys Asp Asn Gln Ser Pro Ala Pro Val Lys Lys Glu Ala Lys Lys Leu
```

```
1               5                   10                  15

Asn Glu Ala Glu
            20

<210> SEQ ID NO 108
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 108

Cys Lys Lys Glu Ala Lys Lys Leu Asn Glu Ala Glu Leu Tyr Asn Lys
1               5                   10                  15

Ile Gln Glu Leu Glu
            20

<210> SEQ ID NO 109
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 109

Cys Glu Leu Tyr Asn Lys Ile Gln Glu Leu Glu Glu Gly Lys Ala Glu
1               5                   10                  15

Leu Phe Asp Lys Leu Glu Lys
            20

<210> SEQ ID NO 110
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 110

Cys Asp Asn Gln Ser Pro Ala Leu Val Lys Lys Glu Ala Lys Lys Leu
1               5                   10                  15

Asn Glu Ala Glu Leu
            20

<210> SEQ ID NO 111
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 111

Cys Asp Asn Gln Ser Pro Ala Pro Ala Pro Val Lys Lys Glu Ala Lys
1               5                   10                  15

Lys Leu Asn Glu Ala Glu
            20

<210> SEQ ID NO 112
<211> LENGTH: 21
<212> TYPE: PRT
<213> ORGANISM: Artificial Sequence
<220> FEATURE:
```

```
<223> OTHER INFORMATION: Description of Artificial Sequence; NOTE =
      Synthetic Construct

<400> SEQUENCE: 112

Cys Gln Glu Leu Glu Glu Gly Lys Ala Glu Leu Phe Asp Lys Leu Glu
1               5                   10                  15

Lys Val Glu Glu Glu
            20

<210> SEQ ID NO 113
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 113

Cys Ala Ala Pro Leu Thr Arg Ala Thr Ala Asp Asn Lys Asp Glu Leu
1               5                   10                  15

Ile Lys Arg Ala Asn Asp
            20

<210> SEQ ID NO 114
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 114

Cys Arg Ala Thr Ala Asp Asn Lys Asp Glu Leu Ile Lys Arg Ala Asn
1               5                   10                  15

Asp Tyr Glu Ile Gln
            20

<210> SEQ ID NO 115
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 115

Cys Glu Ile Gln Asn His Gln Leu Thr Val Glu Asn Lys Lys Leu Lys
1               5                   10                  15

Thr Asp Lys Glu Gln
            20

<210> SEQ ID NO 116
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 116

Cys Arg Ala Thr Ala Asp Asn Lys Asp Glu Leu Ile Lys Arg Ala Asn
1               5                   10                  15

Gly Tyr Glu Ile Gln
            20
```

```
<210> SEQ ID NO 117
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 117

Cys Lys Asp Glu Leu Ile Lys Arg Lys Glu Leu Thr Ile Ile Glu Ile
1               5                   10                  15

Gln Asn His Gln Leu
            20

<210> SEQ ID NO 118
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 118

Cys Asn His Gln Leu Thr Val Glu Asn Lys Lys Leu Lys Thr Asp Lys
1               5                   10                  15

Glu Gln Leu Thr Lys Glu
            20

<210> SEQ ID NO 119
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 119

Cys Asp Ser Ser Arg Glu Val Thr Asn Glu Leu Thr Ala Ser Met Trp
1               5                   10                  15

Lys Ala Gln Ala Asp
            20

<210> SEQ ID NO 120
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 120

Cys Arg Glu Val Thr Asn Glu Leu Thr Ala Ser Met Trp Lys Ala Gln
1               5                   10                  15

Ala Asp Ser Ala Lys
            20

<210> SEQ ID NO 121
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 121
```

Cys Lys Ala Lys Glu Leu Glu Lys Gln Val Glu Glu Tyr Lys Lys Asn
1               5                   10                  15

Tyr Glu Thr Leu Glu Lys
            20

<210> SEQ ID NO 122
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 122

Cys Asp Ser Ser Arg Glu Val Thr Asn Glu Leu Ala Ala Ser Met Trp
1               5                   10                  15

Lys Ala Gln Ala Asp
            20

<210> SEQ ID NO 123
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 123

Cys Asp Ser Ser Arg Asp Ser Ser Arg Glu Val Thr Asn Glu Leu Thr
1               5                   10                  15

Ala Ser Met Trp Lys
            20

<210> SEQ ID NO 124
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 124

Cys Lys Ala Lys Glu Leu Glu Lys Gln Val Glu Glu Tyr Lys Lys Asn
1               5                   10                  15

Tyr Glu Thr Leu Glu Lys
            20

<210> SEQ ID NO 125
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 125

Cys Glu Gln Ala Lys Asn Asn Asn Gly Glu Leu Thr Leu Gln Gln Lys
1               5                   10                  15

Tyr Asp Ala Leu Thr
            20

<210> SEQ ID NO 126
<211> LENGTH: 22
<212> TYPE: PRT
<213> ORGANISM: Artificial Sequence -continued

```
<220> FEATURE:
<223> OTHER INFORMATION: Description of Artificial Sequence; NOTE =
      Synthetic Construct

<400> SEQUENCE: 126

Cys Glu Leu Thr Leu Gln Gln Lys Tyr Asp Ala Leu Thr Asn Glu Asn
1               5                   10                  15

Lys Ser Leu Arg Arg Glu
            20

<210> SEQ ID NO 127
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 127

Cys Asn Glu Asn Lys Ser Leu Arg Arg Glu Arg Asp Asn Tyr Leu Asn
1               5                   10                  15

Tyr Leu Tyr Glu Lys
            20

<210> SEQ ID NO 128
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 128

Cys Arg Arg Glu Arg Asp Asn Tyr Leu Asn Tyr Leu Tyr Glu Lys Glu
1               5                   10                  15

Glu Leu Glu Lys Lys
            20

<210> SEQ ID NO 129
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 129

Cys Ala Asp His Pro Ser Tyr Thr Ala Ala Lys Asp Glu Val Leu Ser
1               5                   10                  15

Lys Phe Ser Val Pro Gly His
            20

<210> SEQ ID NO 130
<211> LENGTH: 21
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 130

Cys Lys Asp Glu Val Leu Ser Lys Phe Ser Val Pro Gly His Val Trp
1               5                   10                  15

Ala His Glu Arg Glu
            20
```

<210> SEQ ID NO 131
<211> LENGTH: 18
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 131

Cys His Glu Arg Glu Lys Asn Asp Lys Leu Ser Ser Glu Asn Glu Gly
1               5                   10                  15

Leu Lys

<210> SEQ ID NO 132
<211> LENGTH: 21
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 132

Cys Asp Lys Leu Arg Leu Glu Lys Glu Glu Leu Lys Thr Asp Leu Gln
1               5                   10                  15

Lys Lys Glu Arg Glu
            20

<210> SEQ ID NO 133
<211> LENGTH: 21
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 133

Cys Lys Asn Asp Lys Leu Ser Ser Glu Asn Glu Gly Leu Lys Ala Gly
1               5                   10                  15

Leu Gln Glu Lys Glu
            20

<210> SEQ ID NO 134
<211> LENGTH: 21
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 134

Cys Glu Gly Asn Ala Arg Leu Ala Gln Ala Gln Glu Glu Ala Leu Arg
1               5                   10                  15

Asp Val Leu Asn Asn
            20

<210> SEQ ID NO 135
<211> LENGTH: 21
<212> TYPE: PRT
<213> ORGANISM: Artificial Sequence
<220> FEATURE:
<223> OTHER INFORMATION: Description of Artificial Sequence; NOTE = Synthetic Construct

<400> SEQUENCE: 135

```
Cys Arg Leu Ala Gln Ala Gln Glu Glu Ala Leu Arg Asp Val Leu Asn
1               5                   10                  15

Asn Thr Pro His Asn
            20

<210> SEQ ID NO 136
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 136

Cys Gln Ala Gln Glu Glu Ala Leu Arg Asp Val Leu Asn Asn Thr Pro
1               5                   10                  15

His Asn Gln Leu Arg Asp
            20

<210> SEQ ID NO 137
<211> LENGTH: 22
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 137

Cys Asp Val Leu Asn Asn Thr Pro His Asn Gln Leu Arg Asp Ala Tyr
1               5                   10                  15

Ala Gly Ala Phe Arg Arg
            20

<210> SEQ ID NO 138
<211> LENGTH: 23
<212> TYPE: PRT
<213> ORGANISM: Artificial Sequence
<220> FEATURE:
<223> OTHER INFORMATION: Description of Artificial Sequence; NOTE =
      Synthetic Construct

<400> SEQUENCE: 138

Cys Gln Leu Arg Asp Pro Tyr Ala Gly Ala Phe Arg Arg Asn Asn Glu
1               5                   10                  15

Leu Glu Lys Ile Ile Gln Glu
            20
```

PEPTIDE VACCINES AGAINST GROUP A STREPTOCOCCI

CROSS REFERENCE TO RELATED APPLICATIONS

This is a continuation of U.S. patent application Ser. No. 10/477,955, filed Mar. 15, 2004, which issued as U.S. Pat. No. 7,407,664. Aug. 5, 2008, which is the §371 National Stage of International Application PCT/US2002/015909, filed May 20, 2002, which claims the benefit of U.S. Provisional Patent Application 60/291,835, filed May 18, 2001.

FIELD OF THE INVENTION

This invention relates generally to immunoreactive molecules, compositions, and methods related thereto. Specifically, those related to Group A Streptococci. More specifically, it relates to synthetic Group A strep immunoreactive peptides, compositions comprising the peptide sequences, vaccines, isolated antibodies elicited by the peptides, kits comprising the peptides or antibodies, and methods of using the peptides, compositions, vaccines and antibodies.

BACKGROUND OF THE INVENTION

Group A streptococci (GAS) are responsible for a wide variety of diseases. These range from uncomplicated pharyngitis to more serious invasive diseases such as necrotizing fasciitis ("flesh eating syndrome") and streptococcal toxic shock syndrome. Additionally, approximately 3% of GAS infections that go untreated will result in acute rheumatic fever. (Brandt, E. R., Good, M. F. 1999. Vaccine strategies to prevent rheumatic fever. Immunol. Res. 19:89-103) All ages are susceptible to GAS attack, but those particularly vulnerable are the elderly, children under 2 years, and African Americans. (Emerging Infections Programs (EIP), supported by the National Center for Infectious Diseases for isolates resulting from active surveillance 1995-1997. California EIP: Arthur Reingold; Connecticut EIP: Matt Carter; Georgia EIP, Monica Farley; Minnesota EIP, Kristine MacDonald; Oregon EIP, Paul Cieslak; Centers for Disease Control and Prevention (CDC), K. O'Brien, B. Beall, K. Deaver-Robinson, R. Facklam, A. Kraus, A. Schuchat, B. Schwartz) Recently, there has been a significant increase in the number of streptococcal infections (Davies, H. D., McGeer, A., Schwartz, B., et al. 1996. Invasive group A streptococcal infections in Ontario, Canada. Ontario group A streptococcal study group. N. Engl. J. Med. 335:547-54) as well as rheumatic fever (Veasey, L. G., Wiedneier, S. W., Osmond, G. S., et al. Resurgence of acute rheumatic fever in the intermountain region of the United States. N. Engl. J. Med. 316:42-7). Based on recent active surveillance, it is estimated that there are approximately 8,500 cases and 1,300 deaths annually in the United States from invasive GAS disease, (EP supported by the National Center for Infectious Diseases for isolates resulting from active surveillance 1995-1997. California EIP: Arthur Reingold; Connecticut EIP: Matt Carter, Georgia EIP, Monica Farley; Minnesota EIP, Kristine MacDonald; Oregon EIP, Paul Cieslak; CDC, K. O'Brien, B. Beall, K. Deaver-Robinson, R. Facklam, A. Kraus, A. Schuchat, B. Schwartz).

A vaccine against GAS could eliminate millions of dollars in health care costs and numerous physician visits.

There are a number of strategies that have been used towards designing an effective streptococcal vaccine (Salvadori L. G., Blake, M. S., McCarty, M., Tai, J. Y., Zabriskie, J. B. 1995. Group A streptococcus-liposome ELISA antibody titers to group A polysaccharide and opsonophagocytic capabilities of the antibodies. J. Infect. Dis. 171:593-600; Ji, Y. Carlson, B., Kondagunta, A., Cleary, P. P. 1997. Intranasal immunization with C5a peptidase prevents nasopharyngeal colonization of mice by group A streptococcus. Infect Immun. 65:2080-2087; Kapur, V. Maffei, J. T., Greer R S., Li, L. L., Adams, G. I., Musser, J M. 1994. Vaccination with streptococcal cysteine protease protects mice against challenge with heterologous group A streptococci. Microb. Pathogenesis. 16:443-450; Dale, J. B., Baird, R. W., Courtney, H. S., Hasty, D. L., Bronze, M. S. 1994. Passive protection of mice against group A streptococcal pharyngeal infection by lipoteichoic acid. J. Infect. Dis. 169:319-323; Dale, J. B., Washburn, R. G., Marques, M. B., Wessels, M. R. 1996. Hyuaronated capsule and surface M protein in resistance to opsonization of group A streptococci. Infect. Immun. 64:1495-1501; Fischetti, V. A. 1989. Streptococcal M protein: molecular design and biological behavior. Clin. Microbiol. 2:285-314; Lancefield, R. C. 1962. Current knowledge of the type-specific M antigens of group A streptococci. J. Immunu 89:307-313; Lancefield, R. C. 1959. Persistence of type-specific antibodies in man following infection with group A streptococci. J. Exp. Med. 110:271-283).

There are difficulties associated with a vaccine strategy involving the M protein, such as the large number of serologic M (emm) types (over 100 serotypes) and the observation that some M proteins contain epitopes that cross-react with human tissues. In addition to the large number of serotypes, every population has a different subset of GAS serotypes which are the most prevalent. In order to deal with these difficulties, different approaches have been tried. For example, observation that the M protein's C-terminus is conserved while the N-terminus is variable has led some workers to try to focus on the C-terminus for broader protection and others to focus on the N-terminus where the most variability is.

Even though some M protein-based vaccines have been designed, for the above reasons, a need still exists for a flexible, effective, multivalent GAS vaccine.

SUMMARY OF THE INVENTION

In accordance with the purpose(s) of this invention, as embodied and broadly described herein, this invention, in one aspect, relates to immunoreactive peptides. In another aspect, it relates to compositions or vaccines comprising the peptides, including polypeptides and proteins.

The synthetic peptides of the invention are approximately 20-25 amino acids in length which are portions of the N termini of the M proteins of the most prevalent United States (U.S.) GAS serotypes and which are immunoreactive. At least some of the synthetic peptides can be recognized by M type-specific antibodies and are capable of eliciting functional opsonic antibodies and/or anti-attachment antibodies without eliciting tissue cross-reactive antibodies.

The invention is also a composition or a vaccine comprised of these synthetic serotype-specific peptides of 20-25 amino acids in length from GAS M proteins. The peptides can be used, for example, individually, in a mixture, or in a polypeptide or protein. Examples of ways the polypeptide or protein can be created include fusing or linking the peptides to each other, synthesizing the polypeptide or protein based on the peptide sequences, and linking or fusing the peptides to a backbone. Also, a liposome may be prepared with the peptides conjugated to it or integrated within it. The compositions or vaccines may further comprise additional components, including but not limited to, carriers, vehicles (e.g., encapsulated, liposomes), and other immune-stimulatory molecules (e.g., adjuvants, other vaccines). Additionally, a DNA vaccine comprising DNA encoding the peptides or compositions of the present invention is disclosed.

The invention may also be isolated antibodies which are elicited in response to the peptides, compositions or vaccines.

In further aspects, the invention also relates to methods for using the peptides, compositions, vaccines, or antibodies and methods for tailoring vaccines. The invention still further relates to kits for using the peptides or antibodies, which can, for example, be used for diagnostic purposes.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawing, which is incorporated in and constitute a part of this specification, illustrates several aspects of the invention and together with the description, serves to explain the principles of the invention.

DESCRIPTION OF THE PREFERRED EMBODIMENTS

Figure 1:
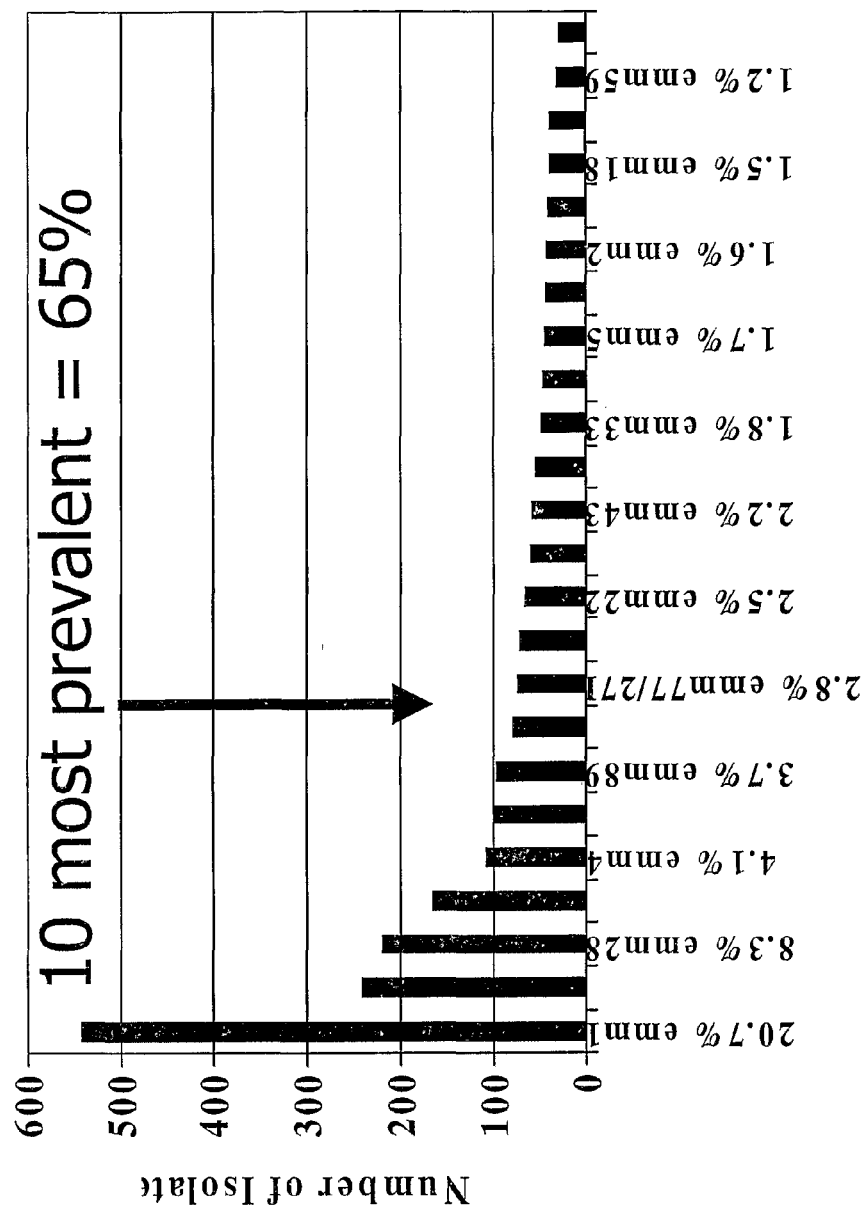
FIG. 1 shows a bar graph of a population-based U.S. sterile site invasive isolate distribution among the 24 most prevalent emm types (2321 (88.9%) of the entire 2612 isolate sample) of Group A strep. The 10 most prevalent isolates (emm1, emm3, emm28, emm12, emm4, emm11, emm89, st2967, emm77/27L, emm6) account for 65% of the disease.

Before the present compounds, compositions, articles, devices, and/or methods are disclosed and described, it is to be understood that this invention is not limited to specific peptides, specific synthetic methods, specific compositions, specific vaccines, specific antibodies, specific kits, specific methods of use, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a peptide" includes mixtures of peptides, reference to "a carrier" includes mixtures of two or more carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

The terms "peptide", "polypeptide" and "protein" are used interchangeably and as used herein refer to more than one amino acid joined by a peptide bond.

"Optional" or "optionally" means that the subsequently described event or circumstance may or may not occur, and that the description includes instances where said event or circumstance occurs and instances where it does not.

By the term "effective amount" of a compound as provided herein is meant a nontoxic but sufficient amount of the compound to provide the desired biological effect. As will be pointed out below, the exact amount required will vary from subject to subject, depending on the species, age, and general condition of the subject, the particular compound used, its mode of administration, and the like. Thus, it is not possible to specify an exact "effective amount." However, an appropriate effective amount may be determined by one of ordinary skill in the art using only routine experimentation.

By "pharmaceutically acceptable" is meant a material that is not biologically or otherwise undesirable, i.e., the material may be administered to an individual without causing any undesirable biological effects or interacting in a deleterious manner with any of the other components of the composition in which it is contained.

"Synthetic" is meant to encompass items, e.g., peptides, which are not naturally occurring, in that they are isolated, synthesized, or otherwise manipulated by man.

"Immunoreactive" as used herein is meant to encompass materials which are capable of reacting with a specific antigen. "Antigenic" and "immunogenic" are terms which fall within the scope of the term "immunoreactive".

"Composition" as used throughout the specification and claims is meant to include any composition of matter, including the peptides, polypeptides, proteins, mixtures, vaccines, antibodies or other forms of matter of the present invention. It is meant to be used generically and interchangeably with the other composition of matter terms, and if used in addition to the other terms, it is used for sake of completeness. "Composition" is a broad term overlapping the coverage of these more specific terms and when used in addition to these more specific terms it is not meant as an indication that it is necessarily different from these more specific terms.

In one aspect, the present invention provides synthetic peptides, compositions, and a vaccine made therefrom and isolated antibodies elicited by administration thereof. The invention also provides methods for using the peptides, compositions, vaccines, or antibodies such as, vaccination of recipients. The invention further provides a method for tailoring vaccines. The invention additionally provides kits for using the peptides or antibodies.

Peptides

The invention is synthetic peptides of approximately 20-25 amino acids in length selected from a section of approximately 45 amino acids from the most N terminal region of the M proteins of the most prevalent U.S. Group A *Streptococcus* (GAS) serotypes which are immunoreactive. At least some of the peptides are capable of eliciting opsonic antibodies and/or anti-attachment antibodies to the GAS serotypes without eliciting tissue cross-reactive antibodies. In one aspect of the invention, the synthetic peptides are from the most prevalent invasive U.S. GAS serotypes which are immunoreactive. The prevalence data in FIG. 1 includes data from invasive isolates. The most frequently occurring invasive types reflect the incidence rate of the same types found in non-invasive isolates. Specific peptides of the present invention are shown below in Table 1. One aspect of the invention is a peptide consisting essentially of the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ED NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ. ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, or SEQ ID NO:138.

Examples of the peptides of the invention, several for each of the 25 most common serotypes (138 peptides), are as follows:

TABLE 1

Synthesized Type-Specific Peptides.

| Seq ID No: | Serotype | Peptide designation | Peptide |
|---|---|---|---|
| 1 | M1 | M1-1 | CNGDGNPREVIEDLAANNPAIQ |
| 2 | | M1-2 | CIQNIRLRHENKDLKARLENA |
| 3 | | M1-3 | CIRLRHENKDLKARLENAMEV |
| 4 | | M1-4 | CNGDGNPREVIEDLAANNPAME |
| 5 | | M1-5 | CIRNIRLRHENKDLKARLENA |
| 6 | | M1-6 | CNGDGNPREVIEDLAANNPVIQ |
| 7 | | M1-7 | CNGDGNPRVVIEDLAANNPAIQ |
| 8 | | M1-8 | CIRLRHHENKDLKARLENAMEV |
| 9 | M2 | M2-1 | CNSKNPVPVKKEAKLSEAELHDK |

TABLE 1-continued

Synthesized Type-Specific Peptides.

| Seq ID No: | Serotype | Peptide designation | Peptide |
|---|---|---|---|
| 10 | | M2-2 | CKKEAKLSEAELHDKIKNLEEEK |
| 11 | | M2-3 | CELHDKIKNLEEEKAELFEKLD |
| 12 | | M2-4 | CELFEKLDKVEEEHKKVEEEHKK |
| 13 | M3 | M3-1 | CDARSVNGEFPRHVKLKNEIE |
| 14 | | M3-2 | CGEFPRHVKLKNEIENLLDQV |
| 15 | | M3-3 | CLDQVTQLYTKHNSNYQQYNA |
| 16 | | M3-4 | CLDQVTQLYNKHNSNYQQYSA |
| 17 | | M3-5 | CLDQVTQLYTKHNSNYQQYSA |
| 18 | | M3-6 | CLNQVTQLYTKHNSNYQQYNA |
| 19 | | M3-7 | CLAQVTQLYTKHNSNYQQYNA |
| 20 | | M3-8 | CLNQVTQLHTKHNSNYQQYNA |
| 21 | | M3-9 | CRSDARSVNGEFPRHVKLKNE |
| 22 | | M3-10 | CQLYTKHIYTKHNSNYQQYNAQ |
| 23 | | M3-11 | CTQLYTKHNSNYQQYNAQAGR |
| 24 | M4 | M4-1 | CAEIKKPQADSAWNWPKEYNA |
| 25 | | M4-2 | CDSAWNWPKEYNALLKENEEL |
| 26 | | M4-3 | CKENEELKVEREKYLSYADDK |
| 27 | | M4-4 | CEELKVEREKYLSYADDKEKDPQ |
| 28 | M11 | M11-1 | CAGQSAPKGTNVSADLYNSLWDE |
| 29 | | M11-2 | CKGTNVSADLYNSLWDENKT |
| 30 | | M11-3 | CDENKTLREKQEEYITKIQNE |
| 31 | | M11-4 | CTEVKAAGQSAPKGTNVSADL |
| 32 | M12 | M12-1 | CDHSDLVAEKQRLEDLGQKFE |
| 33 | | M12-2 | CAEKQRLEDLGQKFERLKQRS |
| 34 | | M12-3 | CLEDLGQKFERLKQRSELYLQ |
| 35 | | M12-4 | CKFERLKQRSELYLHQYYDNK |
| 36 | | M12-5 | CKFERLKRRSELYLQQYYDNK |
| 37 | | M12-6 | CKQRSELYLQQYYDNKSNRYK |
| 38 | | M12-7 | CSELYLQQYYDNKSNGYKGDW |
| 39 | M22 | M22-1 | CESSNNAESSNISQESKLINT |
| 40 | | M22-2 | CESSNISQESKLINTLTDENEK |
| 41 | | M22-3 | CESKLINTLTDENEKLREELQQ |
| 42 | | M22-4 | CNTLNTLTDENEKLREELQQ |
| 43 | | M22-5 | CESSNISQESKLINTLTDENEK |
| 44 | | M22-6 | CEKLREELQQYYALSDAKEEE |
| 45 | M28 | M28-1 | CAESPKSTETSANGADKLAD |
| 46 | | M28-2 | CKSTETSANGADKLADAYNTL |

TABLE 1-continued
Synthesized Type-Specific Peptides.

| Seq ID No: | Serotype | Peptide designation | Peptide |
|---|---|---|---|
| 47 | | M28-3 | CDKLADAYNTLLTEHEKLRDE |
| 48 | | M28-4 | CTEHEKLRDEYYTLIDAKLEEK |
| 49 | | M28-5 | CTEHEKLRDEYYTLIDAKEEE |
| 50 | M77 | M77-1 | CEGVSVGSDASLHNRITDLEEEREK |
| 51 | | M77-2 | CSDASLHNRITDLEEEREKLLNK |
| 52 | | M77-3 | CDLEEEREKLLNKLDKVEEEHKKD |
| 53 | | M77-4 | CDLEEERGKLLNKLDKVEEEHK |
| 54 | | M77-5 | CLNKLDKVEEEHKKDHEQLEK |
| 55 | M89 | M89-1 | CDSDNINRSVSVKDNEKELHNK |
| 56 | | M89-2 | CDNINRSVSVKDNEKELHNKIAD |
| 57 | | M89-3 | CSVKDNEKELHNKIADLEEER |
| 58 | | M89-4 | CELHNEIADLEEERGEHLDKID |
| 59 | | M89-5 | CELHNKIADLEEERGAHLDKID |
| 60 | | M89-6 | CDSDNINRFVSVKDNEKELHN |
| 61 | | M89-7 | CDSDNSDNINRSVSVKDNEKE |
| 62 | | M89-8 | CLEEERGEHLDKIDELKEELK |
| 63 | st2967 | st2967-1 | CNSKNPAPAPASAVPVKKEATK |
| 64 | | st2967-2 | CVPVKKEATKLSEAELYNKIQ |
| 65 | | st2967-3 | CKKEATKLSEAELYNKIQELEE |
| 66 | | st2967-4 | CNSKNPAPAPAVPVKKEATKL |
| 67 | | st2967-5 | CNSKNPAPAVPVKKEATKLSE |
| 68 | | st2967-6 | CAELYNKIQELEEGKAELFDK |
| 69 | M6 | M6-1 | CRVFPRGTVENPDKARELLNK |
| 70 | | M6-2 | CRGTVENPDKARELLNKYDVEN |
| 71 | | M6-3 | CENPDKARELLNKYDVENSMLQ |
| 72 | | M6-4 | CENSMLQANNDNLTDQNKNLTD |
| 73 | | M6-5 | CNSMLQANNDKLTTIENKNLTD |
| 74 | M82 | M82-1 | CDSSSRDITEAGVSKFWKSKFD |
| 75 | | M82-2 | CRDITEAGVSKFWKSKFDAEQN |
| 76 | | M82-3 | CEAGVSKFWKSKFDAEQNRANE |
| 77 | | M82-4 | C DAEQNRANELEKKLSGYEKD |
| 78 | M43 | M43-1 | CEEHPDVVAARESVLNNVR |
| 79 | | M43-2 | CHPDVVAARESVLNNVRVPGT |
| 80 | | M43-3 | CRVPGTLWLRQKEENDKLKLEK |
| 81 | | M43-4 | CLRQKEENDKLKLEKKGLETE |
| 82 | M75 | M75-1 | CEEERTFTELPYEARYKAWKSE |
| 83 | | M75-2 | CELPYEARYKAWKSENDELREN |
| 84 | | M75-3 | CNDELRENYRRTLDKFNTEQ |
| 85 | | M75-4 | CKAWKSENDELRENYRKTLDK |
| 86 | | M75-5 | CRENYRRTLDKFNTEQGKTTR |
| 87 | M33 | M33-1 | CEEHEKVTQAREAVIREMQQR |
| 88 | | M33-2 | CHEKVTQAREAVIREMQQRGT |
| 89 | | M33-3 | CEMQQRGTNFGPLLASTMRDNH |
| 90 | M92 | M92-1 | CDDRSVSTNSGSVSTPYNNLLNE |
| 91 | | M92-2 | CRSVSTNSGSVSTPYNNLLNE |
| 92 | | M92-3 | CEYDDLLAKHGELLSEYDALK |
| 93 | | M92-4 | CDLLAKHGELLSEYDALKEKQDK |
| 94 | M5 | M5-1 | CTVTRGTINDPQRAKEALDKYE |
| 95 | | M5-2 | CDPQRAKEALDKYELENHDLK |
| 96 | | M5-3 | CENHDLKTKNEGLKTENEGLK |
| 97 | | M5-4 | CQRAKAALDKYELENHDLKTKN |
| 98 | | M5-5 | CTVTRGTVNDPQRAKEALDKYE |
| 99 | | M5-6 | CTVTRGTVNDPQRAKETLDKYE |
| 100 | | M5-7 | CTVTRGTINDPQRAKEVIDKYE |
| 101 | | M5-8 | CTVTRSTINDPQRAKEALDKYE |
| 102 | | M5-9 | CHDLKTKNEGLKTENEGLKTEN |
| 103 | M94 (formerly emm13W) | M94-1 | CEEASNNGQLTLQHKNNALTSE |
| 104 | | M94-2 | GQHKNNALTSENESLRREKDR |
| 105 | | M94-3 | CESLRREKDRYLYEKEELEKK |
| 106 | | M94-4 | CRREEKDRYLYEKEELEKKNK |
| 107 | M73 | M73-1 | CDNQSPAPVKKEAKKLNEAE |
| 108 | | M73-2 | CKKEAKKLNEAELYNKIQELE |
| 109 | | M73-3 | CELYNKIQELEEGKAELFDKLEK |
| 110 | | M73-4 | CDNQSPALVKKEAKKLNEAEL |
| 111 | | M73-5 | CDNQSPAPAPVKKEAKKLNEAE |
| 112 | | M73-6 | CQELEEGKAELFDKLEKVEEE |
| 113 | M18 | M18-1 | CAAPLTRATADNKDELIKRAND |
| 114 | | M18-2 | CRATADNKDELIKRANDYEIQ |
| 115 | | M18-3 | CEIQNHQLTVENKKLKTDKEQ |
| 116 | | M18-4 | CRATADNKDELIKRANGYEIQ |
| 117 | | M18-5 | CKDELIKRKELTIIEIQNHQL |
| 118 | | M18-6 | CNHQLTVENKKLKTDKEQLTKE |

TABLE 1-continued

Synthesized Type-Specific Peptides.

| Seq ID No: | Serotype | Peptide designation | Peptide |
|---|---|---|---|
| 119 | M58 | M58-1 | CDSSREVTNELTASMWKAQAD |
| 120 | | M58-2 | CREVTNELTASMWKAQADSAK |
| 121 | | M58-3 | CKAKELEKQVEEYKKNYETLEK |
| 122 | | M58-4 | CDSSREVTNELAASMWKAQAD |
| 123 | | M58-5 | CDSSRDSSREVTNELTASMWK |
| 124 | | M58-6 | CKAKELEKQVEEYKKNYETLEK |
| 125 | M59 | M59-1 | CEQAKNNNGELTLQQKYDALT |
| 126 | | M59-2 | CELTLQQKYDALTNENKSLRRE |
| 127 | | M59-3 | CNENKSLRRERDNYLNYLYEK |
| 128 | | M59-4 | CRRERDNYLNYLYEKEELEKK |
| 129 | M101 (formerly stNS5) | M101-1 | CADHPSYTAAKDEVLSKFSVPGH |
| 130 | | M101-2 | CKDEVLSKFSVPGHVWAHERE |
| 131 | | M101-3 | CHEREKNDKLSSENEGLK |
| 132 | | M101-4 | CDKLRLEKEELKTDLQKKERE |
| 133 | | M101-5 | CKNDKLSSENEGLKAGLQEKE |
| 134 | M41 | M41-1 | CEGNARLAQAQEEALRDVLNN |
| 135 | | M41-2 | CRLAQAQEEALRDVLNNTPHN |
| 136 | | M41-3 | CQAQEEALRDVLNNTPHNQLRD |
| 137 | | M41-4 | CDVLNNTPHNQLRDAYAGAFRR |
| 138 | | M41-5 | CQLRDPYAGAFRRNNELEKIIQE |

It is important to note that a single peptide representing each of the 25 M serotypes represented is predicted to protect against the majority of invasive GAS within each of these serotypes in the U.S. For the majority of these types, the invention provides a peptide that actually matches the sequences of all GAS of these types that we have encountered. We include additional peptides that encompass the extent of M protein gene allelic variation that we have encountered to date within each type from various geographic locations. It is important to note that for the majority of these types, at least one peptide is conserved among all allelic variants that we have encountered.

The small size of the peptides used in the current invention allows a flexible approach for formulating compositions or vaccines. The formulations can be readily and inexpensively changed to account for changes in GAS serotype frequencies in the target population. The adaptability includes frequency changes between populations, years, and the like. Any population for which there is frequency data can have a vaccine formulation customized for it by the methods of the present invention, which are discussed below.

Recently a rapid M protein gene-based subtyping system has been initiated which predicts the type-specific portion of the M protein with very high efficiency. (Beall, B., Facklam, R., Hoenes, T., Schwartz, B. 1997. A survey of emm gene sequences from systemic *Streptococcus pyogenes* infection isolates collected in San Francisco, Calif.; Atlanta, Ga.; and Connecticut state in 1994 and 1995. J. Clin. Microbiol. 35:1231-1235; Beall, B., Facklam, R., Elliot, J., Franklin, A., Hoenes, T., Jackson, D., Laclaire, L., Thompson, T., Viswanathan, P 1998. Streptococcal emm types associated with T-agglutination types and the use of conserved emm restriction fragment patterns for subtyping group A Streptococci. J. Med. Micro. 47:1-6). A Centers for Disease Control and Prevention (CDC) surveillance system used this rapid gene based M subtyping system to gather epidemiological data which showed that the 30 most prevalent invasive serotypes account for approximately 95% of the total invasive isolates in the U.S.

In addition, these peptides should have direct use in formulating vaccines for countries other than the U.S. For example, the 25 serotypes represented in Table 1 also appear to encompass the majority of GAS pediatric pharyngitis isolates in Rome, Italy (91/114=80%), 85% (367/430) of a mixture of sterile and non-sterile GAS isolates recovered in Mexican patients, and 80% (110/137) of primarily invasive isolates recently recovered from patients in Argentina.

It is also important to note that data indicates that these 25 serotypes would have less coverage in other geographic areas such as Malaysia, India, New Guinea, Nepal, and Egypt. For example, out of 136 pharyngitis and impetigo isolates recently recovered in Egypt, only 62 (46%) were of one of these 25 types. While type emm1 is by far the most prevalent type recovered from invasive and noninvasive U.S. isolates (about 20%), only 5/136 (4%) Egypt isolates were type emm1. Thus, the methods of the present invention could be used to tailor vaccines or compositions with the serotypes most prevalent in these areas.

The peptides are synthesized by any of the techniques known in the art, as the method of making them is not critical. One technique is through recombinant methods. Another is manual or automated chemical synthesis using individual amino acids, such as solid phase peptide synthesis. Other methods for synthesizing peptides may be readily apparent to one of ordinary skill in the art.

One of ordinary skill in the art would be able to determine through routine experimentation which of the immunoreactive peptides are capable of eliciting opsonic and/or anti-attachment antibodies.

Though it is known generally in the art that even single substitutions may have a great impact on immunogenicity of a molecule, due to allelic variants which exist for any particular GAS serotype, there are expected to be allowable substitutions within the peptides corresponding with each serotype which maintain immunogenicity. As discussed above, the example peptides in Table 1 include allelic variants of the peptides for a given serotype. For example, up to approximately 3 substitutions within each peptide which correspond with variants of a given serotype may create peptides which also are immunoreactive. That a given substitution results in an immunoreactive peptide can be determined by routine experimentation by making a proposed substitution then testing the immunoreactivity by one of many known assays including those described herein. A variant within a serotype can be identified on the basis of sequence. Any variation within 50 N-terminal residues of mature protein of M protein gene type strain is considered a variant Isolates within an emm type share about ≧84% deduced amino acid sequence identity [as determined by the Wisconsin Package Version 10.1, Genetics Computer Group (GCG), Madison Wis. FASTA program] within the mature amino terminal 45 amino acids compared to the reference type strain sequence. The first three peptides indicated for each serotype in Table 1 are considered to be the peptides from the majority of isolates of the serotype. The additional peptides given in Table 1 for each serotype in some instances represent the majority of isolates in the type, and in other instances represent known variants of these types.

At least some of the individual peptides are capable of protecting a recipient against its corresponding serotype. A composition comprising a mixture of peptides from more than one serotype is able to protect against those corresponding serotypes. A mixture can be tailored such that it contains the most prevalent serotypes in an area (population), thus making the mixture able to protect against the most important serotypes. The tailoring is accomplished by matching the serotype-specific peptides to epidemiological data regarding the prevalence of the serotypes for the population of recipients desired to be protected.

Though each peptide will be immunoreactive for the serotype upon which it is based, the peptides of the present invention may even provide non-serotype-specific effects. It is believed that it is possible that certain prevalent N-terminal fragments may evoke cross-protective opsonic antibodies. This is demonstrated in Example 5 below. It is expected that the present peptides, compositions or vaccines will evoke cross-type opsonization.

Compositions, Vaccines, and Kits

The invention is also polypeptides, proteins, compositions, or vaccines comprising the peptides or sequences of the peptides. The peptides, in addition to being used individually, can be used as a mixture of peptides. One aspect of the invention is a composition comprising the peptides of the present invention as described above. A composition comprising a mixture of peptides is readily prepared by methods well known in the art. Alternatively, to using the peptides individually or in a mixture, the peptides may be joined together into a polypeptide or protein. One aspect of the invention is a polypeptide comprising the sequences of peptides of the present invention. Another aspect of the invention is a protein comprising the sequences of the peptides of the present invention. Standard techniques known in the art may be used to, for example, link the synthesized peptides, synthesize a polypeptide or protein which contains segments corresponding to the desired synthetic peptides, or link the synthetic peptides to a backbone or a liposome. Examples of backbones include, for example, keyhole limpet hemocyanin, bovine serum albumin, tetanus toxoid, diphtheria toxoid, bacterial outer membrane proteins, and artificial amino acid backbones. It is well known to one of ordinary skill in the art how to covalently bond peptides to a backbone or liposome or how to create polypeptides or proteins using recombinant techniques.

As noted above, a vaccine comprising these synthetic peptides is within the scope of the invention. In one aspect, the vaccine comprises an immunogenic amount of the peptide immunogens of the present invention. The data from a CDC surveillance system showing the epidemiological data, as noted above, showed that the 30 most prevalent invasive M types account for approximately 95% of the total invasive isolates in the U.S. An aspect of the present invention is the development of a multi-antigenic peptide (MAP) vaccine representing these most prevalent serotypes. The peptides of the invention may be conveniently formulated into vaccine compositions comprising one or more of the peptides alone or in association with a pharmaceutically acceptable carrier. See, e.g., *Remington's Pharmaceutical Sciences*, latest edition, by E.W. Martin Mack Pub. Co., Easton, Pa., which discloses typical carriers and conventional methods of preparing pharmaceutical compositions that may be used in conjunction with the preparation of formulations of the inventive peptides and which is incorporated by reference herein. A benefit of the vaccine is it can eliminate over 85% of Group A Streptococci infections and reduce by 85% the nasopharyngeal reservoir of Group A Streptococci in the United States with the correct tailoring. The reservoir of GAS is expected to be reduced for the population, not just an individual. Reduction in GAS would have an effect on carriage of the organism, thereby affecting the reservoir in the population. Reduction in carriage of the organism subsequently reduces the exposure rate, thereby increasing herd immunity.

The vaccine comprises and can be made by providing immunogenic amounts of the peptides alone or in a pharmaceutically acceptable vehicle or carrier. Carriers include water, saline, dextrose, and glycerol, for example. The vaccine can further comprise additional immune-stimulatory molecules, including other GAS immunogens, vaccines of other species (such as *H. influenza*, pertussis, *N. meningitidis, pneumococcus*, or *Influenzae*), and adjuvants or mixture of adjuvants. One of ordinary skill in the art would be able to identify vehicles, carriers, other antigens or immunogens, and immunomodulators, such as adjuvants or cytokines, appropriate for the present invention. Additional additives would also be readily apparent to one of skill in the art, such as wetting agents or preservatives.

A DNA vaccine is also within the scope of the present invention. One aspect of the invention is a DNA vaccine comprising DNA encoding immunoreactive peptides or compositions of the present invention. Methods for making DNA sequences suitable for DNA vaccines are known in the art. One of ordinary skill would be able to determine appropriate promoters or other regulatory sequences which may be used in the DNA construct encoding the immunoreactive compositions. DNA vaccines may further comprise other components as in the vaccines and compositions described above and below, such as carriers and agents which increase levels of immunity, such as liposomes. DNA vaccines may be administered by routes similar to other vaccines. Administration of a DNA vaccine results in expression of antigens which produce a protective immune response.

Though the vaccine of the present invention is expected be most effective with multiple serotype-specific peptides, it could contain from one serotype-specific peptide to multiple serotype-specific peptides for every identified serotype of GAS. One of skill in the art would be able to determine the most cost-effective and clinically therapeutic combination based on epidemiological data, using the tailoring method provided herein. In one aspect of the invention, the vaccine contains at least 3 serotype-specific peptides from 3 different serotypes. For example, a vaccine comprising serotype-specific peptides for emm1, emm3, and emm12 is expected to protect against approximately 38% of invasive GAS disease in the U.S. More specifically, this vaccine can comprise the following peptide combinations from Table 1:

| | | | | | | | |
|---|---|---|---|---|---|---|---|
| M1-1 | M1-2 | M1-3 | M1-4 | M1-5 | M1-6 | M1-7 | M1-8 |
| M3-1 | M3-1 | M3-1 | M3-1 | M3-1 | M3-1 | M3-1 | M3-1 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |

-continued

| | | | | | | | |
|---|---|---|---|---|---|---|---|
| M3-2 | M3-2 | M3-2 | M3-2 | M3-2 | M3-2 | M3-2 | M3-2 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-3 | M3-3 | M3-3 | M3-3 | M3-3 | M3-3 | M3-3 | M3-3 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-4 | M3-4 | M3-4 | M3-4 | M3-4 | M3-4 | M3-4 | M3-4 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-5 | M3-5 | M3-5 | M3-5 | M3-5 | M3-5 | M3-5 | M3-5 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-6 | M3-6 | M3-6 | M3-6 | M3-6 | M3-6 | M3-6 | M3-6 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-7 | M3-7 | M3-7 | M3-7 | M3-7 | M3-7 | M3-7 | M3-7 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-8 | M3-8 | M3-8 | M3-8 | M3-8 | M3-8 | M3-8 | M3-8 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-9 | M3-9 | M3-9 | M3-9 | M3-9 | M3-9 | M3-9 | M3-9 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-10 | M3-10 | M3-10 | M3-10 | M3-10 | M3-10 | M3-10 | M3-10 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-11 | M3-11 | M3-11 | M3-11 | M3-11 | M3-11 | M3-11 | M3-11 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-1 | M3-1 | M3-1 | M3-1 | M3-1 | M3-1 | M3-1 | M3-1 |
| M12-2 | M12-2 | M12-2 | M12-2 | M12-2 | M12-2 | M12-2 | M12-2 |
| M1-1 | M1-2 | M1-3 | M1-4 | M1-5 | M1-6 | M1-7 | M1-8 |
| M3-2 | M3-2 | M3-2 | M3-2 | M3-2 | M3-2 | M3-2 | M3-2 |
| M12-2 | M12-2 | M12-2 | M12-2 | M12-2 | M12-2 | M12-2 | M12-2 |
| M1-1 | M1-2 | M1-3 | M1-4 | M1-5 | M1-6 | M1-7 | M1-8 |
| M3-3 | M3-3 | M3-3 | M3-3 | M3-3 | M3-3 | M3-3 | M3-3 |
| M12-2 | M12-2 | M12-2 | M12-2 | M12-2 | M12-2 | M12-2 | M12-2 |
| M1-1 | M1-2 | M1-3 | M1-4 | M1-5 | M1-6 | M1-7 | M1-8 |
| M3-4 | M3-4 | M3-4 | M3-4 | M3-4 | M3-4 | M3-4 | M3-4 |
| M12-2 | M12-2 | M12-2 | M12-2 | M12-2 | M12-2 | M12-2 | M12-2 |
| M1-1 | M1-2 | M1-3 | M1-4 | M1-5 | M1-6 | M1-7 | M1-8 |
| M3-5 | M3-5 | M3-5 | M3-5 | M3-5 | M3-5 | M3-5 | M3-5 |
| M12-2 | M12-2 | M12-2 | M12-2 | M12-2 | M12-2 | M12-2 | M12-2 |
| M1-1 | M1-2 | M1-3 | M1-4 | M1-5 | M1-6 | M1-7 | M1-8 |
| M3-6 | M3-6 | M3-6 | M3-6 | M3-6 | M3-6 | M3-6 | M3-6 |
| M12-2 | M12-2 | M12-2 | M12-2 | M12-2 | M12-2 | M12-2 | M12-2 |
| M1-1 | M1-2 | M1-3 | M1-4 | M1-5 | M1-6 | M1-7 | M1-8 |
| M3-7 | M3-7 | M3-7 | M3-7 | M3-7 | M3-7 | M3-7 | M3-7 |
| M12-2 | M12-2 | M12-2 | M12-2 | M12-2 | M12-2 | M12-2 | M12-2 |
| M1-1 | M1-2 | M1-3 | M1-4 | M1-5 | M1-6 | M1-7 | M1-8 |
| M3-8 | M3-8 | M3-8 | M3-8 | M3-8 | M3-8 | M3-8 | M3-8 |
| M12-2 | M12-2 | M12-2 | M12-2 | M12-1 | M12-2 | M12-2 | M12-2 |
| M1-1 | M1-2 | M1-3 | M1-4 | M1-5 | M1-6 | M1-7 | M1-8 |
| M3-9 | M3-9 | M3-9 | M3-9 | M3-9 | M3-9 | M3-9 | M3-9 |
| M12-2 | M12-2 | M12-2 | M12-2 | M12-2 | M12-2 | M12-2 | M12-2 |
| M1-1 | M1-2 | M1-3 | M1-4 | M1-5 | M1-6 | M1-7 | M1-8 |
| M3-10 | M3-10 | M3-10 | M3-10 | M3-10 | M3-10 | M3-10 | M3-10 |
| M12-2 | M12-2 | M12-2 | M12-2 | M12-2 | M12-2 | M12-2 | M12-2 |
| M1-1 | M1-2 | M1-3 | M1-4 | M1-5 | M1-6 | M1-7 | M1-8 |
| M3-11 | M3-11 | M3-11 | M3-11 | M3-11 | M3-11 | M3-11 | M3-11 |
| M12-2 | M12-2 | M12-2 | M12-2 | M12-2 | M12-2 | M12-2 | M12-2 |
| M1-1 | M1-2 | M1-3 | M1-4 | M1-5 | M1-6 | M1-7 | M1-8 |
| M3-1 | M3-1 | M3-1 | M3-1 | M3-1 | M3-1 | M3-1 | M3-1 |
| M12-3 | M12-3 | M12-3 | M12-3 | M12-3 | M12-3 | M12-3 | M12-3 |
| M1-1 | M1-2 | M1-3 | M1-4 | M1-5 | M1-6 | M1-7 | M1-8 |
| M3-2 | M3-2 | M3-2 | M3-2 | M3-2 | M3-2 | M3-2 | M3-2 |
| M12-3 | M12-3 | M12-3 | M12-3 | M12-3 | M12-3 | M12-3 | M12-3 |
| M1-1 | M1-2 | M1-3 | M1-4 | M1-5 | M1-6 | M1-7 | M1-8 |
| M3-3 | M3-3 | M3-3 | M3-3 | M3-3 | M3-3 | M3-3 | M3-3 |
| M12-3 | M12-3 | M12-3 | M12-3 | M12-3 | M12-3 | M12-3 | M12-3 |
| M1-1 | M1-2 | M1-3 | M1-4 | M1-5 | M1-6 | M1-7 | M1-8 |
| M3-4 | M3-4 | M3-4 | M3-4 | M3-4 | M3-4 | M3-4 | M3-4 |
| M12-3 | M12-3 | M12-3 | M12-3 | M12-3 | M12-3 | M12-3 | M12-3 |
| M1-1 | M1-2 | M1-3 | M1-4 | M1-5 | M1-6 | M1-7 | M1-8 |
| M3-5 | M3-5 | M3-5 | M3-5 | M3-5 | M3-5 | M3-5 | M3-5 |
| M12-3 | M12-3 | M12-3 | M12-3 | M12-3 | M12-3 | M12-3 | M12-3 |
| M1-1 | M1-2 | M1-3 | M1-4 | M1-5 | M1-6 | M1-7 | M1-8 |
| M3-6 | M3-6 | M3-6 | M3-6 | M3-6 | M3-6 | M3-6 | M3-6 |

-continued

| | | | | | | | |
|---|---|---|---|---|---|---|---|
| M12-3 | M12-3 | M12-3 | M12-3 | M12-3 | M12-3 | M12-3 | M12-3 |
| M1-1 | M1-2 | M1-3 | M1-4 | M1-5 | M1-6 | M1-7 | M1-8 |
| M3-7 | M3-7 | M3-7 | M3-7 | M3-7 | M3-7 | M3-7 | M3-7 |
| M12-3 | M12-3 | M12-3 | M12-3 | M12-3 | M12-3 | M12-3 | M12-3 |
| M1-1 | M1-2 | M1-3 | M1-4 | M1-5 | M1-6 | M1-7 | M1-8 |
| M3-8 | M3-8 | M3-8 | M3-8 | M3-8 | M3-8 | M3-8 | M3-8 |
| M12-3 | M12-3 | M12-3 | M12-3 | M12-3 | M12-3 | M12-3 | M12-3 |
| M1-1 | M1-2 | M1-3 | M1-4 | M1-5 | M1-6 | M1-7 | M1-8 |
| M3-9 | M3-9 | M3-9 | M3-9 | M3-9 | M3-9 | M3-9 | M3-9 |
| M12-3 | M12-3 | M12-3 | M12-3 | M12-3 | M12-3 | M12-3 | M12-3 |
| M1-1 | M1-2 | M1-3 | M1-4 | M1-5 | M1-6 | M1-7 | M1-8 |
| M3-10 | M3-10 | M3-10 | M3-10 | M3-10 | M3-10 | M3-10 | M3-10 |
| M12-3 | M12-3 | M12-3 | M12-3 | M12-3 | M12-3 | M12-3 | M12-3 |
| M1-1 | M1-2 | M1-3 | M1-4 | M1-5 | M1-6 | M1-7 | M1-8 |
| M3-11 | M3-11 | M3-11 | M3-11 | M3-11 | M3-11 | M3-11 | M3-11 |
| M12-3 | M12-3 | M12-3 | M12-3 | M12-3 | M12-3 | M12-3 | M12-3 |
| M1-1 | M1-2 | M1-3 | M1-4 | M1-5 | M1-6 | M1-7 | M1-8 |
| M3-1 | M3-1 | M3-1 | M3-1 | M3-1 | M3-1 | M3-1 | M3-1 |
| M12-4 | M12-4 | M12-4 | M12-4 | M12-4 | M12-4 | M12-4 | M12-4 |
| M1-1 | M1-2 | M1-3 | M1-4 | M1-5 | M1-6 | M1-7 | M1-8 |
| M3-2 | M3-2 | M3-2 | M3-2 | M3-2 | M3-2 | M3-2 | M3-2 |
| M12-4 | M12-4 | M12-4 | M12-4 | M12-4 | M12-4 | M12-4 | M12-4 |
| M1-1 | M1-2 | M1-3 | M1-4 | M1-5 | M1-6 | M1-7 | M1-8 |
| M3-3 | M3-3 | M3-3 | M3-3 | M3-3 | M3-3 | M3-3 | M3-3 |
| M12-4 | M12-4 | M12-4 | M12-4 | M12-4 | M12-4 | M12-4 | M12-4 |
| M1-1 | M1-2 | M1-3 | M1-4 | M1-5 | M1-6 | M1-7 | M1-8 |
| M3-4 | M3-4 | M3-4 | M3-4 | M3-4 | M3-4 | M3-4 | M3-4 |
| M12-4 | M12-4 | M12-4 | M12-4 | M12-4 | M12-4 | M12-4 | M12-4 |
| M1-1 | M1-2 | M1-3 | M1-4 | M1-5 | M1-6 | M1-7 | M1-8 |
| M3-5 | M3-5 | M3-5 | M3-5 | M3-5 | M3-5 | M3-5 | M3-5 |
| M12-4 | M12-4 | M12-4 | M12-4 | M12-4 | M12-4 | M12-4 | M12-4 |
| M1-1 | M1-2 | M1-3 | M1-4 | M1-5 | M1-6 | M1-7 | M1-8 |
| M3-6 | M3-6 | M3-6 | M3-6 | M3-6 | M3-6 | M3-6 | M3-6 |
| M12-4 | M12-4 | M12-4 | M12-4 | M12-4 | M12-4 | M12-4 | M12-4 |
| M1-1 | M1-2 | M1-3 | M1-4 | M1-5 | M1-6 | M1-7 | M1-8 |
| M3-7 | M3-7 | M3-7 | M3-7 | M3-7 | M3-7 | M3-7 | M3-7 |
| M12-4 | M12-4 | M12-4 | M12-4 | M12-4 | M12-4 | M12-4 | M12-4 |
| M1-1 | M1-2 | M1-3 | M1-4 | M1-5 | M1-6 | M1-7 | M1-8 |
| M3-8 | M3-8 | M3-8 | M3-8 | M3-8 | M3-8 | M3-8 | M3-8 |
| M12-4 | M12-4 | M12-4 | M12-4 | M12-1 | M12-4 | M12-4 | M12-4 |
| M1-1 | M1-2 | M1-3 | M1-4 | M1-5 | M1-6 | M1-7 | M1-8 |
| M3-9 | M3-9 | M3-9 | M3-9 | M3-9 | M3-9 | M3-9 | M3-9 |
| M12-4 | M12-4 | M12-4 | M12-4 | M12-4 | M12-4 | M12-4 | M12-4 |
| M1-1 | M1-2 | M1-3 | M1-4 | M1-5 | M1-6 | M1-7 | M1-8 |
| M3-10 | M3-10 | M3-10 | M3-10 | M3-10 | M3-10 | M3-10 | M3-10 |
| M12-4 | M12-4 | M12-4 | M12-4 | M12-4 | M12-4 | M12-4 | M12-4 |
| M1-1 | M1-2 | M1-3 | M1-4 | M1-5 | M1-6 | M1-7 | M1-8 |
| M3-11 | M3-11 | M3-11 | M3-11 | M3-11 | M3-11 | M3-11 | M3-11 |
| M12-4 | M12-4 | M12-4 | M12-4 | M12-4 | M12-4 | M12-4 | M12-4 |
| M1-1 | M1-2 | M1-3 | M1-4 | M1-5 | M1-6 | M1-7 | M1-8 |
| M3-1 | M3-1 | M3-1 | M3-1 | M3-1 | M3-1 | M3-1 | M3-1 |
| M12-5 | M12-5 | M12-5 | M12-5 | M12-5 | M12-5 | M12-5 | M12-5 |
| M1-1 | M1-2 | M1-3 | M1-4 | M1-5 | M1-6 | M1-7 | M1-8 |
| M3-2 | M3-2 | M3-2 | M3-2 | M3-2 | M3-2 | M3-2 | M3-2 |
| M12-5 | M12-5 | M12-5 | M12-5 | M12-5 | M12-5 | M12-5 | M12-5 |
| M1-1 | M1-2 | M1-3 | M1-4 | M1-5 | M1-6 | M1-7 | M1-8 |
| M3-3 | M3-3 | M3-3 | M3-3 | M3-3 | M3-3 | M3-3 | M3-3 |
| M12-5 | M12-5 | M12-5 | M12-5 | M12-5 | M12-5 | M12-5 | M12-5 |
| M1-1 | M1-2 | M1-3 | M1-4 | M1-5 | M1-6 | M1-7 | M1-8 |
| M3-4 | M3-4 | M3-4 | M3-4 | M3-4 | M3-4 | M3-4 | M3-4 |
| M12-5 | M12-5 | M12-5 | M12-5 | M12-5 | M12-5 | M12-5 | M12-5 |
| M1-1 | M1-2 | M1-3 | M1-4 | M1-5 | M1-6 | M1-7 | M1-8 |
| M3-5 | M3-5 | M3-5 | M3-5 | M3-5 | M3-5 | M3-5 | M3-5 |
| M12-5 | M12-5 | M12-5 | M12-5 | M12-5 | M12-5 | M12-5 | M12-5 |
| M1-1 | M1-2 | M1-3 | M1-4 | M1-5 | M1-6 | M1-7 | M1-8 |
| M3-6 | M3-6 | M3-6 | M3-6 | M3-6 | M3-6 | M3-6 | M3-6 |
| M12-5 | M12-5 | M12-5 | M12-5 | M12-5 | M12-5 | M12-5 | M12-5 |
| M1-1 | M1-2 | M1-3 | M1-4 | M1-5 | M1-6 | M1-7 | M1-8 |
| M3-7 | M3-7 | M3-7 | M3-7 | M3-7 | M3-7 | M3-7 | M3-7 |
| M12-5 | M12-5 | M12-5 | M12-5 | M12-5 | M12-5 | M12-5 | M12-5 |
| M1-1 | M1-2 | M1-3 | M1-4 | M1-5 | M1-6 | M1-7 | M1-8 |
| M3-8 | M3-8 | M3-8 | M3-8 | M3-8 | M3-8 | M3-8 | M3-8 |
| M12-5 | M12-5 | M12-5 | M12-5 | M12-5 | M12-5 | M12-5 | M12-5 |
| M1-1 | M1-2 | M1-3 | M1-4 | M1-5 | M1-6 | M1-7 | M1-8 |
| M3-9 | M3-9 | M3-9 | M3-9 | M3-9 | M3-9 | M3-9 | M3-9 |
| M12-5 | M12-5 | M12-5 | M12-5 | M12-5 | M12-5 | M12-5 | M12-5 |
| M1-1 | M1-2 | M1-3 | M1-4 | M1-5 | M1-6 | M1-7 | M1-8 |
| M3-10 | M3-10 | M3-10 | M3-10 | M3-10 | M3-10 | M3-10 | M3-10 |
| M12-5 | M12-5 | M12-5 | M12-5 | M12-5 | M12-5 | M12-5 | M12-5 |

-continued

| | | | | | | | |
|---|---|---|---|---|---|---|---|
| M1-1 | M1-2 | M1-3 | M1-4 | M1-5 | M1-6 | M1-7 | M1-8 |
| M3-11 | M3-11 | M3-11 | M3-11 | M3-11 | M3-11 | M3-11 | M3-11 |
| M12-5 | M12-5 | M12-5 | M12-5 | M12-5 | M12-5 | M12-5 | M12-5 |
| M1-1 | M1-2 | M1-3 | M1-4 | M1-5 | M1-6 | M1-7 | M1-8 |
| M3-1 | M3-1 | M3-1 | M3-1 | M3-1 | M3-1 | M3-1 | M3-1 |
| M12-6 | M12-6 | M12-6 | M12-6 | M12-6 | M12-6 | M12-6 | M12-6 |
| M1-1 | M1-2 | M1-3 | M1-4 | M1-5 | M1-6 | M1-7 | M1-8 |
| M3-2 | M3-2 | M3-2 | M3-2 | M3-2 | M3-2 | M3-2 | M3-2 |
| M12-6 | M12-6 | M12-6 | M12-6 | M12-6 | M12-6 | M12-6 | M12-6 |
| M1-1 | M1-2 | M1-3 | M1-4 | M1-5 | M1-6 | M1-7 | M1-8 |
| M3-3 | M3-3 | M3-3 | M3-3 | M3-3 | M3-3 | M3-3 | M3-3 |
| M12-6 | M12-6 | M12-6 | M12-6 | M12-6 | M12-6 | M12-6 | M12-6 |
| M1-1 | M1-2 | M1-3 | M1-4 | M1-5 | M1-6 | M1-7 | M1-8 |
| M3-4 | M3-4 | M3-4 | M3-4 | M3-4 | M3-4 | M3-4 | M3-4 |
| M12-6 | M12-6 | M12-6 | M12-6 | M12-6 | M12-6 | M12-6 | M12-6 |
| M1-1 | M1-2 | M1-3 | M1-4 | M1-5 | M1-6 | M1-7 | M1-8 |
| M3-5 | M3-5 | M3-5 | M3-5 | M3-5 | M3-5 | M3-5 | M3-5 |
| M12-6 | •M12-6 | M12-6 | M12-6 | M12-6 | M12-6 | M12-6 | M12-6 |
| M1-1 | M1-2 | M1-3 | M14 | M1-5 | M1-6 | M1-7 | M1-8 |
| M3-6 | M3-6 | M3-6 | M3-6 | M3-6 | M3-6 | M3-6 | M3-6 |
| M12-6 | M12-6 | M12-6 | M12-6 | M12-6 | M12-6 | M12-6 | M12-6 |
| M1-1 | M1-2 | M1-3 | M1-4 | M1-5 | M1-6 | M1-7 | M1-8 |
| M3-7 | M3-7 | M3-7 | M3-7 | M3-7 | M3-7 | M3-7 | M3-7 |
| M12-6 | M12-6 | M12-6 | M12-6 | M12-6 | M12-6 | M12-6 | M12-6 |
| M1-1 | M1-2 | M1-3 | M1-4 | M1-5 | M1-6 | M1-7 | M1-8 |
| M3-8 | M3-8 | M3-8 | M3-8 | M3-8 | M3-8 | M3-8 | M3-8 |
| M12-6 | M12-6 | M12-6 | M12-6 | M12-1 | M12-6 | M12-6 | M12-6 |
| M1-1 | M1-2 | M1-3 | M1-4 | M1-5 | M1-6 | M1-7 | M1-8 |
| M3-9 | M3-9 | M3-9 | M3-9 | M3-9 | M3-9 | M3-9 | M3-9 |
| M12-6 | M12-6 | M12-6 | M12-6 | M12-6 | M12-6 | M12-6 | M12-6 |
| M1-1 | M1-2 | M1-3 | M1-4 | M1-5 | M1-6 | M1-7 | M1-8 |
| M3-10 | M3-10 | M3-10 | M3-10 | M3-10 | M3-10 | M3-10 | M3-10 |
| M12-6 | M12-6 | M12-6 | M12-6 | M12-6 | M12-6 | M12-6 | M12-6 |
| M1-1 | M1-2 | M1-3 | M1-4 | M1-5 | M1-6 | M1-7 | M1-8 |
| M3-11 | M3-11 | M3-11 | M3-11 | M3-11 | M3-11 | M3-11 | M3-11 |
| M12-6 | M12-6 | M12-6 | M12-6 | M12-6 | M12-6 | M12-6 | M12-6 |
| M1-1 | M1-2 | M1-3 | M1-4 | M1-5 | M1-6 | M1-7 | M1-8 |
| M3-1 | M3-1 | M3-1 | M3-1 | M3-1 | M3-1 | M3-1 | M3-1 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-2 | M3-2 | M3-2 | M3-2 | M3-2 | M3-2 | M3-2 | M3-2 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-3 | M3-3 | M3-3 | M3-3 | M3-3 | M3-3 | M3-3 | M3-3 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-4 | M3-4 | M3-4 | M3-4 | M3-4 | M3-4 | M3-4 | M3-4 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-5 | M3-5 | M3-5 | M3-5 | M3-5 | M3-5 | M3-5 | M3-5 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-6 | M3-6 | M3-6 | M3-6 | M3-6 | M3-6 | M3-6 | M3-6 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-7 | M3-7 | M3-7 | M3-7 | M3-7 | M3-7 | M3-7 | M3-7 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-8 | M3-8 | M3-8 | M3-8 | M3-8 | M3-8 | M3-8 | M3-8 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-9 | M3-9 | M3-9 | M3-9 | M3-9 | M3-9 | M3-9 | M3-9 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-10 | M3-10 | M3-10 | M3-10 | M3-10 | M3-10 | M3-10 | M3-10 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-11 | M3-11 | M3-11 | M3-11 | M3-11 | M3-11 | M3-11 | M3-11 |
| M12-7 | M12-7 | M12-7 | M12-7 | M12-7 | M12-7 | M12-7 | M12-7 |

In another aspect of the invention, the vaccine comprises about 10 serotype-specific peptides, each peptide corresponding to one of the 10 most prevalent serotypes in the U.S., thus making it expected to immunize against approximately 65% of GAS disease in the U.S. More specifically, this vaccine can comprise combinations of 10 peptides wherein one peptide comes from each of the M1, M3, M28, M12, M4, M11, M89, st2967, M77/27L, M6 peptides from Table 1. As demonstrated above, the combinations can be generated and tested according the procedures described in this application to determine those which are effective. In a further aspect of the invention, the vaccine comprises about 30 serotype-specific peptides of the 30 most prevalent serotypes, thus making it expected to immunize against approximately 95% of GAS disease in the U.S. More specifically, this vaccine can comprise combinations of 30 peptides wherein one peptide comes from each of the 30 most prevalent serotypes. As demonstrated above, the combinations can be generated and tested according the procedures described in this application to determine those which are effective. In a still further aspect of the invention, the vaccine can comprise at least one serotype-specific peptide from any identified serotype of GAS. A vaccine covering approximately 60% of GAS disease would be expected to be commercially viable. FIG. 1 shows the most prevalent serotypes in the U.S. currently from which the serotype-specific peptides could be chosen to target. Similar data from any targeted population could be used to tailor the vaccine for the prevalent serotypes and a given percentage of disease. This strategy towards a safe and effective vaccine against GAS offers the advantage of being easily modified to fit the needs of a particular region according to the predominant M types located there.

As indicated above, based on the current epidemiological data, similar serotype-specific peptides would be expected to be effective in vaccines or compositions in the U.S., Italy, Mexico and Argentina, for example. The epidemiological data of Malaysia, India, New Guinea, Nepal and Egypt indicate that vaccines or compositions tailored to these areas may require a different subset of GAS serotype-specific peptides. Based on the teaching herein, such a vaccine is easily within the grasp of the skilled person.

Another strategy for designing a vaccine would be to make it selective for specific GAS illnesses, as all GAS do not cause the same illnesses. For example, the most severe GAS diseases are often considered to be necrotizing fasciitis and toxic shock syndrome which are most frequently caused by M1 and M3. Thus, selecting immunogenic molecules specific to these serotypes would tailor the vaccine to this strategy. More specifically, the combinations could be, for example, muscular injection, by intraperitoneal injection), or the like, although subcutaneous administration is preferred. Though the vaccine is envisioned as an injectable, such as subcutaneous or intramuscularly, the vaccine may be formulated in such a way as to render it mucosally deliverable without the peptides being broken down before providing systemic or mucosal immunity, such as, orally, inhalationally, intranasally, or rectally. The amount of active compound administered will, of course, be dependent, for example, on the subject being treated, the subject's weight, the manner of administration and the judgment of the prescribing physician. Immunogenic amounts can be determined by standard procedures. Examples of other peptide vaccines are known in the art. Dosages of the present invention are expected to be in similar ranges.

Depending on the intended mode of administration, the compositions or vaccines may be in the form of solid, semi-solid or liquid dosage forms, such as, for example, tablets, suppositories, pills, capsules, powders, liquids, suspensions, or the like, preferably in unit dosage form suitable for single administration of a precise dosage. The compositions or vaccines may include, as noted above, an effective amount of the selected immunogens in combination with a pharmaceutically acceptable carrier and, in addition, may include other medicinal agents, pharmaceutical agents, carriers, adjuvants, diluents, etc.

A more recently revised approach for parental administration involves use of a slow release or sustained release system, such that a constant level of dosage is maintained. See, e.g., U.S. Pat. No. 3,710,795, which is incorporated by reference herein. A system using slow release or sustained release may be used with oral administration as well. The vaccine or composition may be administered in liposomes, encapsulated, or otherwise protected or formulated for slower or sustained release.

A subject can be inoculated to generate an active immune response to the presence of the immunogenic composition

| M1-1 | M1-2 | M1-3 | M1-4 | M1-5 | M1-6 | M1-7 | M1-8 |
|---|---|---|---|---|---|---|---|
| M3-1 | M3-1 | M3-1 | M3-1 | M3-1 | M3-1 | M3-1 | M3-1 |
| M1-1 | M1-2 | M1-3 | M1-4 | M1-5 | M1-6 | M1-7 | M1-8 |
| M3-2 | M3-2 | M3-2 | M3-2 | M3-2 | M3-2 | M3-2 | M3-2 |
| M1-1 | M1-2 | M1-3 | M1-4 | M1-5 | M1-6 | M1-7 | M1-8 |
| M3-3 | M3-3 | M3-3 | M3-3 | M3-3 | M3-3 | M3-3 | M3-3 |
| M1-1 | M1-2 | M1-3 | M1-4 | M1-5 | M1-6 | M1-7 | M1-8 |
| M3-4 | M3-4 | M3-4 | M3-4 | M3-4 | M3-4 | M3-4 | M3-4 |
| M1-1 | M1-2 | M1-3 | M1-4 | M1-5 | M1-6 | M1-7 | M1-8 |
| M3-5 | M3-5 | M3-5 | M3-5 | M3-5 | M3-5 | M3-5 | M3-5 |
| M1-1 | M1-2 | M1-3 | M1-4 | M1-5 | M1-6 | M1-7 | M1-8 |
| M3-6 | M3-6 | M3-6 | M3-6 | M3-6 | M3-6 | M3-6 | M3-6 |
| M1-1 | M1-2 | M1-3 | M1-4 | M1-5 | M1-6 | M1-7 | M1-8 |
| M3-7 | M3-7 | M3-7 | M3-7 | M3-7 | M3-7 | M3-7 | M3-7 |
| M1-1 | M1-2 | M1-3 | M1-4 | M1-5 | M1-6 | M1-7 | M1-8 |
| M3-8 | M3-8 | M3-8 | M3-8 | M3-8 | M3-8 | M3-8 | M3-8 |
| M1-1 | M1-2 | M1-3 | M1-4 | M1-5 | M1-6 | M1-7 | M1-8 |
| M3-9 | M3-9 | M3-9 | M3-9 | M3-9 | M3-9 | M3-9 | M3-9 |
| M1-1 | M1-2 | M1-3 | M1-4 | M1-5 | M1-6 | M1-7 | M1-8 |
| M3-10 | M3-10 | M3-10 | M3-10 | M3-10 | M3-10 | M3-10 | M3-10 |
| M1-1 | M1-2 | M1-3 | M1-4 | M1-5 | M1-6 | M1-7 | M1-8 |
| M3-11 | M3-11 | M3-11 | M3-11 | M3-11 | M3-11 | M3-11 | M3-11 |

The peptides, compositions, vaccines or antibodies (discussed below) of the present invention may be administered by any mode of administration capable of delivering a desired dosage to a desired location for a desired biological effect which are known to those of ordinary skill in the art. One of ordinary skill would be able to determine these dosages and routes by routine experimentation. Routes or modes include, for example, orally, parenterally (e.g., intravenously, by intrawhich can later protect the subject from the organism. A passive immune response may be accomplished by any method known in the art.

Kits using peptides or antibodies produced by the present invention may be made. A kit comprises packaging and the antibodies or peptides. A kit may further comprise a solid phase or substrate to which the antibodies or peptides may be attached.

Antibodies

Antibodies are also within the scope of the invention. For example, isolated antibodies which selectively bind with the peptides of the present invention are an aspect of the present invention. These antibodies can be used, for example, in diagnosis, treatment, or vaccination techniques. The antibodies can be monoclonal or specific antibodies. The antibodies can be opsonic antibodies or anti-attachment antibodies. The antibodies are made and isolated by methods well known in the art. Modified antibodies, fragments and humanized antibodies are also within the scope of this invention. It is well known in the art how to make and use modified antibodies, fragments or humanized antibodies.

Methods and Uses

The peptides, compositions, vaccines, and antibodies of the present invention may be used in a variety of applications. For example, preventative/prophylactic, therapeutic, or diagnostic methods; affinity chromatography for separating/purifying antibodies or antigens; active/passive immunotherapy; and use of antibodies generated in passive immunotherapy.

An example of a method of preventing GAS infection comprises administering a prophylactically effective amount of vaccine, or of an anti-idiotype antibody to the peptides of the present invention, to a subject. Also, the antibodies against the peptides of the present invention may be administered in a prophylactically effective amount.

An example of a method of treating a GAS infection comprises administering a therapeutically effective amount of antibodies of the present invention to a subject.

An example of a diagnostic method is determining the serotype of GAS organism responsible for an infection by contacting a sample with multiple serotype-specific antibodies of the present invention and determining which of these serotype-specific antibodies are actually bound with the infecting organism. An example of another diagnostic method is contacting a sample with multiple serotype-specific peptides of the present invention and determining which serotype-specific peptides are actually bound with antibodies in the sample.

A method of measuring the amount of GAS organism in a sample comprising contacting a sample with antibodies of the present invention and measuring the amount of immunocomplexes formed.

Affinity chromatography is frequently used for separating and/or purifying antibodies or antigens. By binding the corresponding antibody or antigen to a substrate, a sample can be passed through a column containing the immunoadsorbent and then the column eluted to collect the isolated corresponding antigen or antibody. More specifically, the peptides of the invention can be bound on a column to purify anti-GAS antibodies. Likewise, anti-GAS antibodies generated in accordance with the invention can be bound to a column and used to purify GAS from a sample.

Immunotherapy is another use for the peptides, compositions, vaccines or antibodies of the present invention. As known in the art, active immunotherapy is achieved by activating a subject's own immune system. By administering the peptides, compositions or vaccines of the present invention, an active immune response may be elicited.

As known in the art, passive immunotherapy is achieved by supplementing a subject's immune system with agents such as antibodies. By administering the antibodies of the present invention, a passive immune response may be elicited.

The method for tailoring vaccines comprises a) identifying a population of recipients for the vaccine; b) gathering prevalence data on serotypes of the targeted organism from a sample within that population of recipients; c) choosing a set of the most prevalent serotypes from the gathered data; d) identifying proteins from the chosen serotypes responsible for evading opsonophagocytosis; e) identifying small peptides within the identified proteins which protect for the chosen serotypes; f) synthesizing the identified peptides; g) formulating a vaccine comprising the peptides identified in step e). Specifically, the small peptides may be those of about 20-25 amino acids and protection may be by elicitation of opsonic or anti-attachment antibodies.

Other uses for or variations of the above methods using the above peptides, compositions, vaccines or antibodies may be readily apparent to one of ordinary skill in the art.

The approach of employing a mixture of defined synthetic N terminal M protein segments protecting against prevalent U.S. Group A streptococcal (GAS) strains will favorably compare against any of the prior art approaches. The present approach has found excellent immunogenicity and type-specific opsonic antibody titers with the peptides assessed. Animal studies have indicated that individual peptides protect in a type-specific manner not only against systemic infection, but against nasopharyngeal carriage of GAS. Many N terminal M protein segments have already been demonstrated to not evoke antibodies cross-reactive with human tissues. There is no evidence that chemically linking the current peptides to carriers or backbones will increase the risk of undesirable cross reactions. The methodology can be proven for each of the most common M types found in U.S. invasive disease isolates. The strategy can be expanded to less frequently occurring GAS types. This allows the vaccine to be quickly and precisely adapted to changes in individual strain frequencies in a given geographic area or demographic population by addition or deletion of individual peptide components.

EXAMPLES

Experimental

The following examples are put forth so as to provide those of ordinary skill in the art with a complete disclosure and description of how the compounds, compositions, articles, devices, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric.

Materials and Methods

A CDC surveillance system used a rapid gene-based M subtyping system to gather epidemiological data and showed that the 30 most prevalent invasive M types account for approximately 95% of the total invasive isolates in the U.S.

Peptide Synthesis and Purification

Synthetic peptides (approximately 20-25-mers), representing epitopes of the most prevalent GAS M types were synthesized. Their sequences were derived from the M protein N-terminal region that confers type-specific immunity.

Peptides were synthesized on a Model ACT396 Omega multiple peptide synthesizer (Advanced Chemtech, Louisville, Ky.) by Fmoc-chemistry using a HOBT/DIC strategy with double couplings. Matrix-assisted laser desorption/ionization, time-of-flight mass spectroscopy (MALDI-TOF MS)

(Bruker REFLEX, Billerica, Mass.) was utilized to determine the mass to charge (m/z) of the crude peptides.

Abbreviations
Fmoc (9-fluorenylmethyloxycarbonyl)
HOBT (1-hydroxybenzotriazole)
DIC (Diisopropylcarbodiimide)

Enzyme-Linked Immunosorbent Assay (ELISA)

Overlapping peptides representing each M type were assessed for their immunogenicity using ELISA and dot-immunoblot.

Levels of anti-M protein antibodies in mouse sera were determined by an enzyme-linked immunosorbent assay (ELISA) using either synthetic peptides or whole M protein as antigen. Microtiter plates (DYNEX Immulon 2 HB) were coated with 10 µg/ml antigen in 10 mM phosphate-buffered saline (PBS) at 4° C. overnight. Plates were rinsed three times with wash buffer (0.05% Tween 20 in 10 mM PBS, pH 7.2) and blocked with 1% BSA in PBS for one hour at 37° C. The appropriate test sera were applied at a starting dilution of 1:1000 and serially diluted two fold down the plate in PBS. Plates were incubated at 37° C. for 30 minutes and subsequently rinsed three times. Goat anti-rabbit or goat anti-mouse Ig-peroxidase conjugate diluted 1:10,000 in PBS was added to all wells and incubated for two hours at 37° C. Plates were rinsed three times with wash buffer and freshly prepared TMB peroxidase (Kirkegaard and Perry Laboratories) was added. Reactions were quenched with 0.18 M $H_2SO_4$ after 30 minutes at room temperature and $OD_{450}$ was measured with a Labsystems Multiskan plate reader using Ascent software. ELISA titers are expressed as the reciprocal of the last dilution which gave a reading $OD_{450}$>0.10.

Immunization

Mice (6 week old female Swiss Webster, Harley-Sprague) were immunized subcutaneously (s.c.) with either the peptide in alum or alum alone for control groups. Peptides were rotated in the alum mixture for 2 hours at 4° C. and stored at 4° C. overnight prior to use. Initial injections (100 µl) consisted of 50 µg peptide in alum (25 µg for M3-2 peptide) with identical booster injections given at 2 and 4 weeks (except for the M3-2 peptide which was only given as an initial dose and single booster at 2 weeks).

Opsonophagocytosis

Opsonophagocytosis assays were performed as previously described in Lancefield, R. C., Persistence of type-specific antibodies in man following infection with group A streptococci, 1959, J. Immunol., 89:307. Briefly, diluted serum (50 µl) was added to mid-log phase GAS ($10^3$ CFU) in Todd-Hewitt broth (50 µl) and whole, heparinized blood (500 µl) from a nonopsonic human donor. Mixtures were briefly vortexed and placed at 37° C. in a shaker for 3 hours. Dilutions were then plated on trypticase soy agar plates (5% sheep blood) to quantitate viable organisms. The % killing is expressed as [(CFU control−CFU test)/CFU control]×100.

NP Challenge

Mice were challenged intranasally one week after the final booster injection was administered. Prior to being challenged, mice were anesthetized with a ketamine/xylazine mixture. Mice were then given $10^4$-$10^5$ CFU (10 µl) of streptococci intranasally via a microliter pipette. They were sacrificed 24 hours after the challenge and the nasopharyngeal passages were washed with approximately 100 µl physiological saline which was collected and immediately placed on ice. Dilutions of the wash were then plated on trypticase soy agar plates (5% sheep blood) and incubated at 37° C. for 18 hours to quantitate viable organisms. Nasopharyngeal colonization in immunized mice was compared to non-immunized controls. Statistical analysis of the NP data was accomplished using the t-test and rank sum test.

Detection of Heart Cross-Reactive Antibodies

Mouse sera were screened for heart cross-reactive antibodies with an indirect immunofluorescence assay (IFA). Glass slides containing formaline-fixed human heart tissue were deparaffinized before use and stored in $dH_2O$. Slides were air-dried 10 minutes and incubated in a moist chamber with 1:500 mouse test sera at room temperature for 30 minutes. Slides were rinsed and soaked in PBS for 5 minutes. Slides were then incubated in a moist chamber with 1:500 goat anti-mouse FITC-labeled globulin at room temperature for 30 minutes. Slides were washed as described previously and allowed to air-dry. One drop of mounting fluid (DAKO) was applied to each slide followed by a glass cover slip (Corning 24×40 mm). Slides were immediately examined under a fluorescent microscope. The positive control was a 1:500 mouse anticlonal antibody to human HLA (Caltag).

Example 1

Peptide Recognition by Anti M-Protein Rabbit Sera

The immunoreactivity of several synthetic peptides was determined by ELISA using rabbit sera prepared against whole M protein. The synthetic peptides are representative of relatively small portions of the M protein N-terminus; therefore, it was advantageous to determine if the epitopes contained within particular peptides were immunoreactive with sera prepared against whole M protein. It was shown that the whole anti-M protein rabbit sera of the respective serotypes could bind to each of the synthetic peptides within that serotype. However, some peptides were more highly immunoreactive than others, thus being better suited for use in the animal studies. The peptides showing the highest reactivity in each serotype group tested were M1-4, M3-2 and M12-1. This indicated that immunoreactive epitopes were contained within the amino acid sequences of the synthetic peptides.

The immunoreactivity of peptides with SEQ ID NO:1, SEQ ID NO:2, SEQ ID NO:3, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ BD NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138 are confirmed by ELISA using rabbit sera prepared against whole M protein.

Example 2

Immunogenicity of Synthetic Peptides in Swiss Webster Mice

Studies were then carried out in vivo in a mouse model to determine the ability of the tested synthetic peptides to protect against GAS challenge and to evaluate their immunogenicity as a single MAP formulation.

Mice were immunized s.c. with selected peptides using aluminum hydroxide or aluminum phosphate as an adjuvant. Serology results indicated that aluminum hydroxide elicited higher antibody levels and, therefore, it was used for all subsequent immunizations. ELISA indicated that antibodies were elicited to the M type peptides.

TABLE 2

ELISA results determining elicitation of antibodies.

| Peptide | ELISA |
|---|---|
| M1-4 | no |
| M1-2 | no |
| M1-3 | yes |
| M3-1 | yes |
| M3-2 | yes |
| M3-4 | no |
| M12-1 | yes |
| M12-2 | yes (weak) |
| M12-3 | no |

Five of the nine synthetic peptides shown in Table 2 were able to elicit an antibody response, with each of the three serotypes under investigation being represented by at least one immunogenic peptide. The titers of the immunogenic peptides were as follows:

TABLE 3

Titers of the immunogenic peptides in immunized mice.

| Peptide | Titer |
|---|---|
| M1-3 | 1:16,000 |
| M3-1 | 1:8,000 |
| M3-2 | 1:160,000 |
| M12-1 | 1:160,000 |
| M12-2 | 1:1000 |

Mice are immunized s.c. with peptides and various combinations of peptides with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138.

ELISA is used to confirm antibody elicitation to at least some of the peptides and peptide combinations. Titers are determined for the peptides and combinations of peptides.

Example 3

Opsonophagocytosis

The mouse sera that were shown to contain anti-M antibodies by the ELISA assay were then tested for functional activity with the in vitro opsonophagocytosis assay (Lancefield 1959), Table 4. Each of the sera tested positive in the assay and was able to reduce the amount of viable bacteria relative to controls. The values for the reduction of bacteria in the opsonophagocytosis assays were as shown in Table 5.

TABLE 4

Sera results for opsonophagocytosis assay.

| Peptide | Opsono (in vitro) |
|---|---|
| M1-4 | nd |
| M1-2 | nd |
| M1-3 | yes |
| M3-1 | yes |
| M3-2 | yes |
| M3-4 | nd |
| M12-1 | yes |

TABLE 4-continued

Sera results for opsonophagocytosis assay.

| Peptide | Opsono (in vitro) |
|---|---|
| M12-2 | nd |
| M12-3 | nd |

TABLE 5

Percentage reduction of viable GAS bacteria.

| Peptide | Reduction |
|---|---|
| M1-3 | 50% |
| M3-1 | 80-90% |
| M3-2 | 60-80% |
| M12-1 | 70-80% |

It is interesting to note that within the M3 serotype, while the M3-1 peptide induced an antibody response that was more than a magnitude lower than that of the M3-2 peptide, it was able to opsonophagocytize bacteria more effectively.

Mouse sera is tested that is shown to contain anti-M antibodies from the peptides and combinations of peptides selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138 for functional activity with an in vitro opsonophagocytosis assay. The sera test positive in the assay and are able to reduce the amount of viable bacteria relative to controls.

Example 4

Nasopharyngeal Colonization Challenge

Nasopharyngeal (NP) colonization challenge experiments were performed on mice vaccinated (s.c.) with either M3-1 or M3-2 peptide in alum in comparison to control animals which received alum only. The nasopharyngeal colonization challenge was performed by doing a nasal wash 24 hours after challenge. The subjects were administered $10^4$ CFUs 1 week after final boost. Dilutions of the wash were plated. Both peptides were able to induce an effective in vivo immune response that reduced colonization in the vaccinated group relative to the unvaccinated group.

TABLE 6

Reduction of nasopharyngeal colonization in vaccinated mice relative to control mice.

| Peptide | Reduction of colonization | P |
|---|---|---|
| M3-1 | 87% | P = 0.010 |
| M3-2 | 67% | P = 0.029 |

The M3-1 peptide reduced NP colonization by 87% (P<0.010), while the M3-2 peptide was able to reduce NP colonization by 67% (P<0.029) relative to the control group. No deaths were recorded in any group. To our knowledge this is the first example of in vivo reduction of nasopharyngeal colonization of GAS bacteria by immunization with a type-specific synthetic peptide.

NP colonization challenges are performed on mice vaccinated s.c. with the peptides and peptide combinations selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ED NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:11, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, and SEQ ID NO:138. Peptides and peptide combinations are confirmed to induce an effective in vivo immune response that reduced colonization in the vaccinated group relative to the unvaccinated group. No deaths are reported in any group.

Example 5

Cross-Type Protection by Peptides

Some of the peptides tested in the previous examples were tested for cross-type protection using the methods described above. Table 7 shows in vitro data on reduction in bacteria versus a control. The peptide tested and serotype against which it was tested is indicated. This example clearly shows that peptides M3-1 and M3-2 were able to significantly reduce M43 type bacteria in addition to M3 type bacteria.

TABLE 7

Functional antibody bactericidal activity in vitro showing cross-protection against heterologous M type.

| Peptide | GAS M type used in assay | % CFU reduction |
|---|---|---|
| M1-3 | M1 | 80-95% |
| M3-1 | M3 | 70-90% |
| M3-2 | M3 | 90-95% |
| M12-1 | M12 | 70-80% |
| M3-1 | M43 | 80-90% |
| M3-2 | M43 | 60-80% |

Some of the peptides were tested for reduction of colonization of GAS in mice. The second line of data shows mice immunized with peptides M1-3, M3-2 and M12-1. The peptides were administered together but were not chemically combined in any way. The third line of data shows mice that were inoculated with M3-2. Some of the mice were colonized by M3, and some of the mice were colonized by M43. The % CFU reduction is the reduction overall for the mice which received M3-2. This again demonstrates that M3-2 was capable in vivo of cross-type protection.

TABLE 8

Reduction of colonization in mice.

| Peptides | Colonizing GAS M type | % CFU reduction (P value) |
|---|---|---|
| M1-3 | M1 | 90% (P < 0.10) |
| M1-3, M3-2, M12-1 | M1 | 74% (P < 0.25) |
| M3-2 | M3 or M43 | 67% (P < 0.30) |

The cross-type protection is confirmed for peptides and peptide combinations selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:11, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, and SEQ ID NO:138. Reductions in bacteria are shown in vitro and in vivo.

Example 6

Detection of Heart Cross-Reactive Antibodies

Mouse immune sera that contained functional antibody were examined for the presence of heart cross-reactive antibodies with an IFA. The mouse sera were tested in parallel with a positive control, mouse monoclonal antibody to human leukocyte antigen (HLA). None of the anti-M peptide sera from immunized mice reacted with the heart tissue.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A composition comprising a polypeptide comprising the amino acid sequence of SEQ ID NO: 14.

2. The composition of claim 1, wherein the polypeptide is a chimeric fusion protein.

3. The composition of claim 2, wherein the chimeric fusion protein comprises an amino acid sequence of one or more heterologous Group A *Streptococcus* (GAS) M-type peptides.

4. The composition of claim 1, wherein the polypeptide is linked to a peptide backbone.

5. The composition of claim 1, further comprising a pharmaceutically acceptable vehicle or carrier.

6. The composition of claim 1, further comprising additional immune-stimulatory molecules.

7. The composition of claim 6, wherein the additional immune-stimulatory molecules comprise GAS-based peptides.

8. The composition of claim 7, wherein the additional immune-stimulatory molecules comprise non-GAS vaccines/immunogens selected from the group consisting of *Hemophilus* influenza, pertussis, *N. meningitidis*, pneumococcus, and *Influenzae*.

9. The composition of claim 6, wherein the additional immune-stimulatory molecules comprise adjuvants.

10. The composition of claim 1, wherein the polypeptide consists essentially of the amino acid sequence of SEQ ID NO: 14.

11. The composition of claim 1, wherein the polypeptide consists of the amino acid sequence of SEQ ID NO: 14.

12. An immunogenic composition for eliciting a protective immune response to Group A *Streptococcus* comprising an immunogenic amount of the composition according to claim 1.

13. The immunogenic composition of claim 12, wherein the immunogenic composition is capable of eliciting functional opsonic antibodies and does not contain epitopes that cross-react with tissues.

14. The immunogenic composition of claim 12, wherein the immunogenic composition is effective in decreasing the nasopharyngeal reservoir of GAS when administered.

15. A method for inducing an immune response against the emm3 serotype of Group A *Streptococcus* comprising administering an immunogenic amount of the immunogenic composition of claim 1 to a subject.

16. The method of claim 15, wherein the administration is via injection.

17. The method of claim 15, wherein the administration is via a mucosal delivery method.

18. The method of claim 15, wherein the immune response induces opsonic antibodies.

19. An isolated polypeptide comprising the amino acid sequence of SEQ ID NO: 14.

20. The polypeptide of claim 19, wherein the polypeptide is a chimeric fusion protein.

21. The polypeptide of claim 20, wherein the chimeric fusion protein comprises an amino acid sequence of one or more heterologous Group A *Streptococcus* (GAS) M-type peptides.

22. The isolated polypeptide of claim 19, wherein the polypeptide consists essentially of the amino acid sequence of SEQ ID NO: 14.

23. The isolated polypeptide of claim 19, wherein the polypeptide consists of the amino acid sequence of SEQ ID NO: 14.

* * * * *

UNITED STATES PATENT AND TRADEMARK OFFICE
CERTIFICATE OF CORRECTION

PATENT NO.        : 7,883,710 B2
APPLICATION NO.   : 12/144461
DATED             : February 8, 2011
INVENTOR(S)       : Bernard W. Beall et al.

It is certified that error appears in the above-identified patent and that said Letters Patent is hereby corrected as shown below:

On the Cover, Section (73) Assignee:
"Health and Human Services" should read --Health and Human Services, Centers for Disease Control and Prevention--.

On the Cover, Section (56) under OTHER PUBLICATIONS:
Page 1, right column, "patters" should read --patterns--.

Page 1, right column, "89-1031" should read --89-103--.

Column 1, line 9, "664. Aug." should read --664, Aug.--.

Column 1, line 34, "103)" should read --103).--.

Column 1, line 44, "Schwartz)" should read --Schwartz).--.

Column 1, line 55, "EP" should read --EIP--.

Column 2, line 7, "G.I." should read --G.J.--.

Column 2, line 21, "Immunu" should read --Immun.--.

Column 2, line 67 to Column 3, line 1, "encapsulated, liposomes" should read --encapsulated liposomes--.

Column 3, line 26, "constitute" should read --constitutes--.

Column 5, line 7, "SEQ ED NO:27" should read --SEQ ID NO:27--.

Column 7, line 51, "TTIEN" should read --TTEN--.

Signed and Sealed this
Third Day of July, 2012

David J. Kappos
*Director of the United States Patent and Trademark Office*

CERTIFICATE OF CORRECTION (continued)
U.S. Pat. No. 7,883,710 B2

Column 8, line 44, "GQHK" should read --CQHK--.

Column 10, line 7, "P 1998" should read --R. 1998--.

Column 10, line 63, "variant Isolates" should read --variant. Isolates--.

Column 12, line 46, "is expected be" should read --is expected to be--.

Column 19, line 7, "according the" should read --according to the--.

Column 20, line 26, "parental" should read --parenteral--.

Column 21, line 23, "anti-idotype" should read --anti-idiotype--.

Column 21, line 42, "comprising" should read --comprises--.

Column 23, line 21, "two fold" should read --two-fold--.

Column 24, line 56, "SEQ BD NO:52" should read --SEQ ID NO:52--.

Column 28, line 41-42, "SEQ ED NO:11" should read --SEQ ID NO:11--.

Column 29, line 3, "SEQ ID NO:11" should read --SEQ ID NO:111--.

Column 30, line 31, "SEQ ID NO:11" should read --SEQ ID NO:111--.

Table, column 12, line 60 to column 17, line 59 should read as follows:

| M1-1 | M1-2 | M1-3 | M1-4 | M1-5 | M1-6 | M1-7 | M1-8 |
|---|---|---|---|---|---|---|---|
| M3-1 | M3-1 | M3-1 | M3-1 | M3-1 | M3-1 | M3-1 | M3-1 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-2 | M3-2 | M3-2 | M3-2 | M3-2 | M3-2 | M3-2 | M3-2 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-3 | M3-3 | M3-3 | M3-3 | M3-3 | M3-3 | M3-3 | M3-3 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-4 | M3-4 | M3-4 | M3-4 | M3-4 | M3-4 | M3-4 | M3-4 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-5 | M3-5 | M3-5 | M3-5 | M3-5 | M3-5 | M3-5 | M3-5 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-6 | M3-6 | M3-6 | M3-6 | M3-6 | M3-6 | M3-6 | M3-6 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-7 | M3-7 | M3-7 | M3-7 | M3-7 | M3-7 | M3-7 | M3-7 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-8 | M3-8 | M3-8 | M3-8 | M3-8 | M3-8 | M3-8 | M3-8 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-9 | M3-9 | M3-9 | M3-9 | M3-9 | M3-9 | M3-9 | M3-9 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-10 | M3-10 | M3-10 | M3-10 | M3-10 | M3-10 | M3-10 | M3-10 |
| M12-1 | M12-1 | M12-1 | M12-1 | M12-1 | M12-1 | M12-1 | M12-1 |
| M1-1 | M1-2 | M1-3 | M1-4 | M1-5 | M1-6 | M1-7 | M1-8 |
| M3-11 | M3-11 | M3-11 | M3-11 | M3-11 | M3-11 | M3-11 | M3-11 |
| M12-1 | M12-1 | M12-1 | M12-1 | M12-1 | M12-1 | M12-1 | M12-1 |

| M1-1 | M1-2 | M1-3 | M1-4 | M1-5 | M1-6 | M1-7 | M1-8 |
|---|---|---|---|---|---|---|---|
| M3-1 | M3-1 | M3-1 | M3-1 | M3-1 | M3-1 | M3-1 | M3-1 |
| M12-2 | M12-2 | M12-2 | M12-2 | M12-2 | M12-2 | M12-2 | M12-2 |
| M1-1 | M1-2 | M1-3 | M1-4 | M1-5 | M1-6 | M1-7 | M1-8 |
| M3-2 | M3-2 | M3-2 | M3-2 | M3-2 | M3-2 | M3-2 | M3-2 |
| M12-2 | M12-2 | M12-2 | M12-2 | M12-2 | M12-2 | M12-2 | M12-2 |
| M1-1 | M1-2 | M1-3 | M1-4 | M1-5 | M1-6 | M1-7 | M1-8 |
| M3-3 | M3-3 | M3-3 | M3-3 | M3-3 | M3-3 | M3-3 | M3-3 |
| M12-2 | M12-2 | M12-2 | M12-2 | M12-2 | M12-2 | M12-2 | M12-2 |
| M1-1 | M1-2 | M1-3 | M1-4 | M1-5 | M1-6 | M1-7 | M1-8 |
| M3-4 | M3-4 | M3-4 | M3-4 | M3-4 | M3-4 | M3-4 | M3-4 |
| M12-2 | M12-2 | M12-2 | M12-2 | M12-2 | M12-2 | M12-2 | M12-2 |
| M1-1 | M1-2 | M1-3 | M1-4 | M1-5 | M1-6 | M1-7 | M1-8 |
| M3-5 | M3-5 | M3-5 | M3-5 | M3-5 | M3-5 | M3-5 | M3-5 |
| M12-2 | M12-2 | M12-2 | M12-2 | M12-2 | M12-2 | M12-2 | M12-2 |

| M1-1    | M1-2    | M1-3    | M1-4    | M1-5    | M1-6    | M1-7    | M1-8    |
| M3-6    | M3-6    | M3-6    | M3-6    | M3-6    | M3-6    | M3-6    | M3-6    |
| M12-2   | M12-2   | M12-2   | M12-2   | M12-2   | M12-2   | M12-2   | M12-2   |
| M1-1    | M1-2    | M1-3    | M1-4    | M1-5    | M1-6    | M1-7    | M1-8    |
| M3-7    | M3-7    | M3-7    | M3-7    | M3-7    | M3-7    | M3-7    | M3-7    |
| M12-2   | M12-2   | M12-2   | M12-2   | M12-2   | M12-2   | M12-2   | M12-2   |
| M1-1    | M1-2    | M1-3    | M1-4    | M1-5    | M1-6    | M1-7    | M1-8    |
| M3-8    | M3-8    | M3-8    | M3-8    | M3-8    | M3-8    | M3-8    | M3-8    |
| M12-2   | M12-2   | M12-2   | M12-2   | M12-1   | M12-2   | M12-2   | M12-2   |
| M1-1    | M1-2    | M1-3    | M1-4    | M1-5    | M1-6    | M1-7    | M1-8    |
| M3-9    | M3-9    | M3-9    | M3-9    | M3-9    | M3-9    | M3-9    | M3-9    |
| M12-2   | M12-2   | M12-2   | M12-2   | M12-2   | M12-2   | M12-2   | M12-2   |
| M1-1    | M1-2    | M1-3    | M1-4    | M1-5    | M1-6    | M1-7    | M1-8    |
| M3-10   | M3-10   | M3-10   | M3-10   | M3-10   | M3-10   | M3-10   | M3-10   |
| M12-2   | M12-2   | M12-2   | M12-2   | M12-2   | M12-2   | M12-2   | M12-2   |
| M1-1    | M1-2    | M1-3    | M1-4    | M1-5    | M1-6    | M1-7    | M1-8    |
| M3-11   | M3-11   | M3-11   | M3-11   | M3-11   | M3-11   | M3-11   | M3-11   |
| M12-2   | M12-2   | M12-2   | M12-2   | M12-2   | M12-2   | M12-2   | M12-2   |

| M1-1    | M1-2    | M1-3    | M1-4    | M1-5    | M1-6    | M1-7    | M1-8    |
| M3-1    | M3-1    | M3-1    | M3-1    | M3-1    | M3-1    | M3-1    | M3-1    |
| M12-3   | M12-3   | M12-3   | M12-3   | M12-3   | M12-3   | M12-3   | M12-3   |
| M1-1    | M1-2    | M1-3    | M1-4    | M1-5    | M1-6    | M1-7    | M1-8    |
| M3-2    | M3-2    | M3-2    | M3-2    | M3-2    | M3-2    | M3-2    | M3-2    |
| M12-3   | M12-3   | M12-3   | M12-3   | M12-3   | M12-3   | M12-3   | M12-3   |
| M1-1    | M1-2    | M1-3    | M1-4    | M1-5    | M1-6    | M1-7    | M1-8    |
| M3-3    | M3-3    | M3-3    | M3-3    | M3-3    | M3-3    | M3-3    | M3-3    |
| M12-3   | M12-3   | M12-3   | M12-3   | M12-3   | M12-3   | M12-3   | M12-3   |
| M1-1    | M1-2    | M1-3    | M1-4    | M1-5    | M1-6    | M1-7    | M1-8    |
| M3-4    | M3-4    | M3-4    | M3-4    | M3-4    | M3-4    | M3-4    | M3-4    |
| M12-3   | M12-3   | M12-3   | M12-3   | M12-3   | M12-3   | M12-3   | M12-3   |
| M1-1    | M1-2    | M1-3    | M1-4    | M1-5    | M1-6    | M1-7    | M1-8    |
| M3-5    | M3-5    | M3-5    | M3-5    | M3-5    | M3-5    | M3-5    | M3-5    |
| M12-3   | M12-3   | M12-3   | M12-3   | M12-3   | M12-3   | M12-3   | M12-3   |
| M1-1    | M1-2    | M1-3    | M1-4    | M1-5    | M1-6    | M1-7    | M1-8    |
| M3-6    | M3-6    | M3-6    | M3-6    | M3-6    | M3-6    | M3-6    | M3-6    |
| M12-3   | M12-3   | M12-3   | M12-3   | M12-3   | M12-3   | M12-3   | M12-3   |
| M1-1    | M1-2    | M1-3    | M1-4    | M1-5    | M1-6    | M1-7    | M1-8    |
| M3-7    | M3-7    | M3-7    | M3-7    | M3-7    | M3-7    | M3-7    | M3-7    |
| M12-3   | M12-3   | M12-3   | M12-3   | M12-3   | M12-3   | M12-3   | M12-3   |
| M1-1    | M1-2    | M1-3    | M1-4    | M1-5    | M1-6    | M1-7    | M1-8    |
| M3-8    | M3-8    | M3-8    | M3-8    | M3-8    | M3-8    | M3-8    | M3-8    |
| M12-3   | M12-3   | M12-3   | M12-3   | M12-3   | M12-3   | M12-3   | M12-3   |
| M1-1    | M1-2    | M1-3    | M1-4    | M1-5    | M1-6    | M1-7    | M1-8    |
| M3-9    | M3-9    | M3-9    | M3-9    | M3-9    | M3-9    | M3-9    | M3-9    |
| M12-3   | M12-3   | M12-3   | M12-3   | M12-3   | M12-3   | M12-3   | M12-3   |
| M1-1    | M1-2    | M1-3    | M1-4    | M1-5    | M1-6    | M1-7    | M1-8    |
| M3-10   | M3-10   | M3-10   | M3-10   | M3-10   | M3-10   | M3-10   | M3-10   |
| M12-3   | M12-3   | M12-3   | M12-3   | M12-3   | M12-3   | M12-3   | M12-3   |

| M1-1 | M1-2 | M1-3 | M1-4 | M1-5 | M1-6 | M1-7 | M1-8 |
|------|------|------|------|------|------|------|------|
| M3-11 | M3-11 | M3-11 | M3-11 | M3-11 | M3-11 | M3-11 | M3-11 |
| M12-3 | M12-3 | M12-3 | M12-3 | M12-3 | M12-3 | M12-3 | M12-3 |

| M1-1 | M1-2 | M1-3 | M1-4 | M1-5 | M1-6 | M1-7 | M1-8 |
|------|------|------|------|------|------|------|------|
| M3-1 | M3-1 | M3-1 | M3-1 | M3-1 | M3-1 | M3-1 | M3-1 |
| M12-4 | M12-4 | M12-4 | M12-4 | M12-4 | M12-4 | M12-4 | M12-4 |
| M1-1 | M1-2 | M1-3 | M1-4 | M1-5 | M1-6 | M1-7 | M1-8 |
| M3-2 | M3-2 | M3-2 | M3-2 | M3-2 | M3-2 | M3-2 | M3-2 |
| M12-4 | M12-4 | M12-4 | M12-4 | M12-4 | M12-4 | M12-4 | M12-4 |
| M1-1 | M1-2 | M1-3 | M1-4 | M1-5 | M1-6 | M1-7 | M1-8 |
| M3-3 | M3-3 | M3-3 | M3-3 | M3-3 | M3-3 | M3-3 | M3-3 |
| M12-4 | M12-4 | M12-4 | M12-4 | M12-4 | M12-4 | M12-4 | M12-4 |
| M1-1 | M1-2 | M1-3 | M1-4 | M1-5 | M1-6 | M1-7 | M1-8 |
| M3-4 | M3-4 | M3-4 | M3-4 | M3-4 | M3-4 | M3-4 | M3-4 |
| M12-4 | M12-4 | M12-4 | M12-4 | M12-4 | M12-4 | M12-4 | M12-4 |
| M1-1 | M1-2 | M1-3 | M1-4 | M1-5 | M1-6 | M1-7 | M1-8 |
| M3-5 | M3-5 | M3-5 | M3-5 | M3-5 | M3-5 | M3-5 | M3-5 |
| M12-4 | M12-4 | M12-4 | M12-4 | M12-4 | M12-4 | M12-4 | M12-4 |
| M1-1 | M1-2 | M1-3 | M1-4 | M1-5 | M1-6 | M1-7 | M1-8 |
| M3-6 | M3-6 | M3-6 | M3-6 | M3-6 | M3-6 | M3-6 | M3-6 |
| M12-4 | M12-4 | M12-4 | M12-4 | M12-4 | M12-4 | M12-4 | M12-4 |
| M1-1 | M1-2 | M1-3 | M1-4 | M1-5 | M1-6 | M1-7 | M1-8 |
| M3-7 | M3-7 | M3-7 | M3-7 | M3-7 | M3-7 | M3-7 | M3-7 |
| M12-4 | M12-4 | M12-4 | M12-4 | M12-4 | M12-4 | M12-4 | M12-4 |
| M1-1 | M1-2 | M1-3 | M1-4 | M1-5 | M1-6 | M1-7 | M1-8 |
| M3-8 | M3-8 | M3-8 | M3-8 | M3-8 | M3-8 | M3-8 | M3-8 |
| M12-4 | M12-4 | M12-4 | M12-4 | M12-1 | M12-4 | M12-4 | M12-4 |
| M1-1 | M1-2 | M1-3 | M1-4 | M1-5 | M1-6 | M1-7 | M1-8 |
| M3-9 | M3-9 | M3-9 | M3-9 | M3-9 | M3-9 | M3-9 | M3-9 |
| M12-4 | M12-4 | M12-4 | M12-4 | M12-4 | M12-4 | M12-4 | M12-4 |
| M1-1 | M1-2 | M1-3 | M1-4 | M1-5 | M1-6 | M1-7 | M1-8 |
| M3-10 | M3-10 | M3-10 | M3-10 | M3-10 | M3-10 | M3-10 | M3-10 |
| M12-4 | M12-4 | M12-4 | M12-4 | M12-4 | M12-4 | M12-4 | M12-4 |
| M1-1 | M1-2 | M1-3 | M1-4 | M1-5 | M1-6 | M1-7 | M1-8 |
| M3-11 | M3-11 | M3-11 | M3-11 | M3-11 | M3-11 | M3-11 | M3-11 |
| M12-4 | M12-4 | M12-4 | M12-4 | M12-4 | M12-4 | M12-4 | M12-4 |

| M1-1 | M1-2 | M1-3 | M1-4 | M1-5 | M1-6 | M1-7 | M1-8 |
|------|------|------|------|------|------|------|------|
| M3-1 | M3-1 | M3-1 | M3-1 | M3-1 | M3-1 | M3-1 | M3-1 |
| M12-5 | M12-5 | M12-5 | M12-5 | M12-5 | M12-5 | M12-5 | M12-5 |
| M1-1 | M1-2 | M1-3 | M1-4 | M1-5 | M1-6 | M1-7 | M1-8 |
| M3-2 | M3-2 | M3-2 | M3-2 | M3-2 | M3-2 | M3-2 | M3-2 |
| M12-5 | M12-5 | M12-5 | M12-5 | M12-5 | M12-5 | M12-5 | M12-5 |
| M1-1 | M1-2 | M1-3 | M1-4 | M1-5 | M1-6 | M1-7 | M1-8 |
| M3-3 | M3-3 | M3-3 | M3-3 | M3-3 | M3-3 | M3-3 | M3-3 |
| M12-5 | M12-5 | M12-5 | M12-5 | M12-5 | M12-5 | M12-5 | M12-5 |
| M1-1 | M1-2 | M1-3 | M1-4 | M1-5 | M1-6 | M1-7 | M1-8 |
| M3-4 | M3-4 | M3-4 | M3-4 | M3-4 | M3-4 | M3-4 | M3-4 |
| M12-5 | M12-5 | M12-5 | M12-5 | M12-5 | M12-5 | M12-5 | M12-5 |

| M1-1 | M1-2 | M1-3 | M1-4 | M1-5 | M1-6 | M1-7 | M1-8 |
|---|---|---|---|---|---|---|---|
| M3-5 | M3-5 | M3-5 | M3-5 | M3-5 | M3-5 | M3-5 | M3-5 |
| M12-5 | M12-5 | M12-5 | M12-5 | M12-5 | M12-5 | M12-5 | M12-5 |
| M1-1 | M1-2 | M1-3 | M1-4 | M1-5 | M1-6 | M1-7 | M1-8 |
| M3-6 | M3-6 | M3-6 | M3-6 | M3-6 | M3-6 | M3-6 | M3-6 |
| M12-5 | M12-5 | M12-5 | M12-5 | M12-5 | M12-5 | M12-5 | M12-5 |
| M1-1 | M1-2 | M1-3 | M1-4 | M1-5 | M1-6 | M1-7 | M1-8 |
| M3-7 | M3-7 | M3-7 | M3-7 | M3-7 | M3-7 | M3-7 | M3-7 |
| M12-5 | M12-5 | M12-5 | M12-5 | M12-5 | M12-5 | M12-5 | M12-5 |
| M1-1 | M1-2 | M1-3 | M1-4 | M1-5 | M1-6 | M1-7 | M1-8 |
| M3-8 | M3-8 | M3-8 | M3-8 | M3-8 | M3-8 | M3-8 | M3-8 |
| M12-5 | M12-5 | M12-5 | M12-5 | M12-5 | M12-5 | M12-5 | M12-5 |
| M1-1 | M1-2 | M1-3 | M1-4 | M1-5 | M1-6 | M1-7 | M1-8 |
| M3-9 | M3-9 | M3-9 | M3-9 | M3-9 | M3-9 | M3-9 | M3-9 |
| M12-5 | M12-5 | M12-5 | M12-5 | M12-5 | M12-5 | M12-5 | M12-5 |
| M1-1 | M1-2 | M1-3 | M1-4 | M1-5 | M1-6 | M1-7 | M1-8 |
| M3-10 | M3-10 | M3-10 | M3-10 | M3-10 | M3-10 | M3-10 | M3-10 |
| M12-5 | M12-5 | M12-5 | M12-5 | M12-5 | M12-5 | M12-5 | M12-5 |
| M1-1 | M1-2 | M1-3 | M1-4 | M1-5 | M1-6 | M1-7 | M1-8 |
| M3-11 | M3-11 | M3-11 | M3-11 | M3-11 | M3-11 | M3-11 | M3-11 |
| M12-5 | M12-5 | M12-5 | M12-5 | M12-5 | M12-5 | M12-5 | M12-5 |

| M1-1 | M1-2 | M1-3 | M1-4 | M1-5 | M1-6 | M1-7 | M1-8 |
|---|---|---|---|---|---|---|---|
| M3-1 | M3-1 | M3-1 | M3-1 | M3-1 | M3-1 | M3-1 | M3-1 |
| M12-6 | M12-6 | M12-6 | M12-6 | M12-6 | M12-6 | M12-6 | M12-6 |
| M1-1 | M1-2 | M1-3 | M1-4 | M1-5 | M1-6 | M1-7 | M1-8 |
| M3-2 | M3-2 | M3-2 | M3-2 | M3-2 | M3-2 | M3-2 | M3-2 |
| M12-6 | M12-6 | M12-6 | M12-6 | M12-6 | M12-6 | M12-6 | M12-6 |
| M1-1 | M1-2 | M1-3 | M1-4 | M1-5 | M1-6 | M1-7 | M1-8 |
| M3-3 | M3-3 | M3-3 | M3-3 | M3-3 | M3-3 | M3-3 | M3-3 |
| M12-6 | M12-6 | M12-6 | M12-6 | M12-6 | M12-6 | M12-6 | M12-6 |
| M1-1 | M1-2 | M1-3 | M1-4 | M1-5 | M1-6 | M1-7 | M1-8 |
| M3-4 | M3-4 | M3-4 | M3-4 | M3-4 | M3-4 | M3-4 | M3-4 |
| M12-6 | M12-6 | M12-6 | M12-6 | M12-6 | M12-6 | M12-6 | M12-6 |
| M1-1 | M1-2 | M1-3 | M1-4 | M1-5 | M1-6 | M1-7 | M1-8 |
| M3-5 | M3-5 | M3-5 | M3-5 | M3-5 | M3-5 | M3-5 | M3-5 |
| M12-6 | M12-6 | M12-6 | M12-6 | M12-6 | M12-6 | M12-6 | M12-6 |
| M1-1 | M1-2 | M1-3 | M1-4 | M1-5 | M1-6 | M1-7 | M1-8 |
| M3-6 | M3-6 | M3-6 | M3-6 | M3-6 | M3-6 | M3-6 | M3-6 |
| M12-6 | M12-6 | M12-6 | M12-6 | M12-6 | M12-6 | M12-6 | M12-6 |
| M1-1 | M1-2 | M1-3 | M1-4 | M1-5 | M1-6 | M1-7 | M1-8 |
| M3-7 | M3-7 | M3-7 | M3-7 | M3-7 | M3-7 | M3-7 | M3-7 |
| M12-6 | M12-6 | M12-6 | M12-6 | M12-6 | M12-6 | M12-6 | M12-6 |
| M1-1 | M1-2 | M1-3 | M1-4 | M1-5 | M1-6 | M1-7 | M1-8 |
| M3-8 | M3-8 | M3-8 | M3-8 | M3-8 | M3-8 | M3-8 | M3-8 |
| M12-6 | M12-6 | M12-6 | M12-6 | M12-1 | M12-6 | M12-6 | M12-6 |
| M1-1 | M1-2 | M1-3 | M1-4 | M1-5 | M1-6 | M1-7 | M1-8 |
| M3-9 | M3-9 | M3-9 | M3-9 | M3-9 | M3-9 | M3-9 | M3-9 |
| M12-6 | M12-6 | M12-6 | M12-6 | M12-6 | M12-6 | M12-6 | M12-6 |

| M1-1 | M1-2 | M1-3 | M1-4 | M1-5 | M1-6 | M1-7 | M1-8 |
|------|------|------|------|------|------|------|------|
| M3-10 | M3-10 | M3-10 | M3-10 | M3-10 | M3-10 | M3-10 | M3-10 |
| M12-6 | M12-6 | M12-6 | M12-6 | M12-6 | M12-6 | M12-6 | M12-6 |
| M1-1 | M1-2 | M1-3 | M1-4 | M1-5 | M1-6 | M1-7 | M1-8 |
| M3-11 | M3-11 | M3-11 | M3-11 | M3-11 | M3-11 | M3-11 | M3-11 |
| M12-6 | M12-6 | M12-6 | M12-6 | M12-6 | M12-6 | M12-6 | M12-6 |

| M1-1 | M1-2 | M1-3 | M1-4 | M1-5 | M1-6 | M1-7 | M1-8 |
|------|------|------|------|------|------|------|------|
| M3-1 | M3-1 | M3-1 | M3-1 | M3-1 | M3-1 | M3-1 | M3-1 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-2 | M3-2 | M3-2 | M3-2 | M3-2 | M3-2 | M3-2 | M3-2 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-3 | M3-3 | M3-3 | M3-3 | M3-3 | M3-3 | M3-3 | M3-3 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-4 | M3-4 | M3-4 | M3-4 | M3-4 | M3-4 | M3-4 | M3-4 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-5 | M3-5 | M3-5 | M3-5 | M3-5 | M3-5 | M3-5 | M3-5 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-6 | M3-6 | M3-6 | M3-6 | M3-6 | M3-6 | M3-6 | M3-6 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-7 | M3-7 | M3-7 | M3-7 | M3-7 | M3-7 | M3-7 | M3-7 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-8 | M3-8 | M3-8 | M3-8 | M3-8 | M3-8 | M3-8 | M3-8 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-9 | M3-9 | M3-9 | M3-9 | M3-9 | M3-9 | M3-9 | M3-9 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-10 | M3-10 | M3-10 | M3-10 | M3-10 | M3-10 | M3-10 | M3-10 |
| M12-7 | M12-7 | M12-7 | M12-7 | M12-7 | M12-7 | M12-7 | M12-7 |
| M1-1 | M1-2 | M1-3 | M1-4 | M1-5 | M1-6 | M1-7 | M1-8 |
| M3-11 | M3-11 | M3-11 | M3-11 | M3-11 | M3-11 | M3-11 | M3-11 |
| M12-7 | M12-7 | M12-7 | M12-7 | M12-7 | M12-7 | M12-7 | M12-7 |

CERTIFICATE OF CORRECTION (continued)
U.S. Pat. No. 7,883,710 B2

Table, column 19, lines 37-59 should read as follows:

| M1-1 M3-1 | M1-2 M3-1 | M1-3 M3-1 | M1-4 M3-1 | M1-5 M3-1 | M1-6 M3-1 | M1-7 M3-1 | M1-8 M3-1 |
|---|---|---|---|---|---|---|---|
| M1-1 M3-2 | M1-2 M3-2 | M1-3 M3-2 | M1-4 M3-2 | M1-5 M3-2 | M1-6 M3-2 | M1-7 M3-2 | M1-8 M3-2 |
| M1-1 M3-3 | M1-2 M3-3 | M1-3 M3-3 | M1-4 M3-3 | M1-5 M3-3 | M1-6 M3-3 | M1-7 M3-3 | M1-8 M3-3 |

| M1-1 M3-4 | M1-2 M3-4 | M1-3 M3-4 | M1-4 M3-4 | M1-5 M3-4 | M1-6 M3-4 | M1-7 M3-4 | M1-8 M3-4 |
|---|---|---|---|---|---|---|---|
| M1-1 M3-5 | M1-2 M3-5 | M1-3 M3-5 | M1-4 M3-5 | M1-5 M3-5 | M1-6 M3-5 | M1-7 M3-5 | M1-8 M3-5 |
| M1-1 M3-6 | M1-2 M3-6 | M1-3 M3-6 | M1-4 M3-6 | M1-5 M3-6 | M1-6 M3-6 | M1-7 M3-6 | M1-8 M3-6 |
| M1-1 M3-7 | M1-2 M3-7 | M1-3 M3-7 | M1-4 M3-7 | M1-5 M3-7 | M1-6 M3-7 | M1-7 M3-7 | M1-8 M3-7 |
| M1-1 M3-8 | M1-2 M3-8 | M1-3 M3-8 | M1-4 M3-8 | M1-5 M3-8 | M1-6 M3-8 | M1-7 M3-8 | M1-8 M3-8 |
| M1-1 M3-9 | M1-2 M3-9 | M1-3 M3-9 | M1-4 M3-9 | M1-5 M3-9 | M1-6 M3-9 | M1-7 M3-9 | M1-8 M3-9 |
| M1-1 M3-10 | M1-2 M3-10 | M1-3 M3-10 | M1-4 M3-10 | M1-5 M3-10 | M1-6 M3-10 | M1-7 M3-10 | M1-8 M3-10 |
| M1-1 M3-11 | M1-2 M3-11 | M1-3 M3-11 | M1-4 M3-11 | M1-5 M3-11 | M1-6 M3-11 | M1-7 M3-11 | M1-8 M3-11 |